(12) United States Patent
Magoon et al.

(10) Patent No.: US 11,170,450 B1
(45) Date of Patent: Nov. 9, 2021

(54) MACHINE-LEARNING DRIVEN REAL-TIME DATA ANALYSIS

(71) Applicant: Nayya Health, Inc., New York, NY (US)

(72) Inventors: Akash Magoon, Fallston, MD (US); Aman Magoon, Fallston, MD (US); John Joseph Glorioso, Jr., Laurel, MD (US); Sina Chehrazi, New York, NY (US)

(73) Assignee: Nayya Health, Inc., New York, NY (US)

(*) Notice: Subject to any disclaimer, the term of this patent is extended or adjusted under 35 U.S.C. 154(b) by 0 days.

(21) Appl. No.: 17/228,975

(22) Filed: Apr. 13, 2021

(51) Int. Cl.
*G06Q 40/08* (2012.01)
*G06N 20/00* (2019.01)
(Continued)

(52) U.S. Cl.
CPC .............. *G06Q 40/08* (2013.01); *G06N 5/04* (2013.01); *G06N 20/00* (2019.01); *G06Q 10/10* (2013.01);
(Continued)

(58) Field of Classification Search
CPC ........ G06Q 40/08; G06Q 10/10; G16H 40/20; G16H 10/60; G16H 50/20; G16H 20/10; G06N 20/00; G06N 5/04
(Continued)

(56) References Cited

U.S. PATENT DOCUMENTS

| 7,853,459 B2 | 12/2010 | Kay |
| 8,930,228 B1 | 1/2015 | Ball |

(Continued)

FOREIGN PATENT DOCUMENTS

WO   2008057761 A3   5/2008

OTHER PUBLICATIONS

Malhotra et al.; "Machine Learning in Insurance"; Accenture; 2018; pp. 1-13; located at https://www.accenture.com/_acnmedia/pdf-84/accenture-machine-leaning-insurance.pdf.
(Continued)

*Primary Examiner* — Michael Tomaszewski
(74) *Attorney, Agent, or Firm* — NovoTechIP International PLLC

(57) ABSTRACT

A data processing system for insurance claims analysis and adjudication implements obtaining policy coverage information for each of a plurality of insurance policies and insurance claim information associated with an insured user, analyzing the insurance claim information using a first machine learning model to identify an occurrence of a first type of event and a first group of insurance claims associated with the first type of event; analyzing the first group of insurance claims, the policy information, and an indication of the first type of event using a second machine learning model to obtain a prediction whether a respective insurance policy will cover the first insurance claim; and responsive to determining that the respective insurance policy will cover the first insurance claim, causing a user interface to be presented on a display of a computing device associated with the insured user to guide the insured user through submitting the first insurance claim to an insurance provider associated with the respective insurance policy.

17 Claims, 21 Drawing Sheets

(51) Int. Cl.
*G06N 5/04* (2006.01)
*G16H 50/20* (2018.01)
*G16H 10/60* (2018.01)
*G16H 40/20* (2018.01)
*G06Q 10/10* (2012.01)
*G16H 20/10* (2018.01)

(52) U.S. Cl.
CPC ............. *G16H 10/60* (2018.01); *G16H 40/20* (2018.01); *G16H 50/20* (2018.01); *G16H 20/10* (2018.01)

(58) Field of Classification Search
USPC .......................................................... 705/2–3
See application file for complete search history.

(56) References Cited

U.S. PATENT DOCUMENTS

| | | | |
|---|---|---|---|
| 9,183,593 B2 | 11/2015 | Willis et al. | |
| 9,495,700 B2 | 11/2016 | Hoch et al. | |
| 10,395,006 B2 | 8/2019 | Brown | |
| 10,803,528 B2 | 10/2020 | Mdeway | |
| 10,818,395 B1* | 10/2020 | Khalak | G06Q 30/0251 |
| 2004/0111302 A1* | 6/2004 | Falk | G06Q 40/02 705/4 |
| 2009/0281841 A1* | 11/2009 | Basak | G06Q 40/08 705/4 |
| 2009/0287509 A1* | 11/2009 | Basak | G06Q 10/10 705/4 |
| 2018/0089379 A1* | 3/2018 | Collins | G06Q 10/1057 |
| 2019/0005198 A1* | 1/2019 | Richards | G06Q 10/10 |
| 2021/0035225 A1* | 2/2021 | Simpson | G06N 5/04 |

OTHER PUBLICATIONS

Sahu et al.; "Automating claims adjudication workflows using Amazon Textract and Amazon Comprehend Medical"; AWS for Industries; Nov. 19, 2019; pp. 1-11; located at https://aws.amazon.com/blogs/industries/automating-claims-adjudication-workflows-using-amazon-textract-and-amazon-comprehend-medical/.

* cited by examiner

AllInsurance

Please enter your login credentials.

Online ID
_____

Password
_____

Forgot password?

By selecting "Submit" you are agreeing to our Terms of Service.

Cancel    Submit

AllInsurance

Where would you like us to send your security code?

○ Text    XXX-XXX-5525

○ Email   tr.....@gmail.com

Cancel    Continue

AllInsurance

Please verify the security code that was sent to
XXX-XXX-5525:

6   1   3   3

Cancel    Verify

Success

You can now access your policy information and claims for your AllInsurace policy.

[ Close ]

Act on Today's Claim Opportunities

| Save up to | Anna by submitting your urgent care |
|---|---|
| $247 | claim dated October 2, 2020 to AllInsure |

[ Save Now ]

Claims Overview

| Service Date | Member | Type | Provider | Description | You Pay |
|---|---|---|---|---|---|
| Oct 1, 2020 | Jeff | Medical | Dr. Bhatnagar | Orthopedic Consult | $211.50 |
| Sep 23, 2020 | Anna | Dental | Dr. Garcia | Preventative Visit | $25 |
| Sep 23, 2020 | Jeff | Pharmacy | CVS Pharmacy | Prescription | $25 copay |
| Sep 19, 2020 | David | Medical | Dr. Gau | Urgent Care Visit | $412.44 |
| Sep 15, 2020 | Anna | Pharmacy | CVS Pharmacy | Prescription | $10.81 |
| Sep 11, 2020 | Jeff | Medical | Dr. Bhatnagar | Orthopedic Consult | $57.21 |
| Sept 10, 2020 | Jeff | Pharmacy | CVS Pharmacy | Prescription | $10.81 |

Claims Analytics

Costs Overview
Total Spend $684.75

Medical
Pharmacy   15%
Dental     7%

Total Spend $684.75

Medical Breakdown 66%

| Specialist Visits $41.23 | Diagnostics $54.12 |
|---|---|
| Urgent Care $352.36 | Primary Care $98.64 |
| Inpatient Facility $97.43 | Outpatient Facility $69.60 |

FIG. 6A

Claims Opportunities

Save up to $247

Anna by submitting your urgent care claim dated October 2, 2020 to AllInsure

You paid $453 recently in out-of-pocket expenses.

Orthopedic consult with Dr. Arun Bhatnagar on October 1, 2020

Please answer a few questions to find out whether your recent orthopedic visit qualifies for a claim with your AllInsurance Accident Insurance Policy.

Begin >

Cost Breakdown for Claim 99887771092

| Service Date | Claim Number | Provider | | Plan Paid |
|---|---|---|---|---|
| October 1, 2020 | 99887771092 | Dr. Arun Bhatnagar | | $692.12 |
| Member | Claim Received | Description | | You Paid |
| James Oldham | Not Available | Orthopedic Consult | | $211.50 |
| Type | Claim Status | Provider Address | | |
| Medical | Approved 01/21/2021 | 1122 Main Street #112, Laurel, MD 20707 | | |

| Service | Code(s) | Billed by Provider | Plan Discount | Allowed by Plan | Plan Paid | You Paid |
|---|---|---|---|---|---|---|
| Laboratory General Service 12231 | 21912D 59783A | $30.00 | $20.32 | $9.68 | $0.00 | $9.68 |
| Laboratory General Service 12231D1 | 21912E 597881 | $35.00 | $22.84 | $12.16 | $0.00 | $12.16 |
| Laboratory General Service 12231D1 | 21912E 597881 | $35.00 | $22.84 | $12.16 | $0.00 | $12.16 |
| Laboratory General Service 12231D1 | 21912E 597881 | $28.00 | $19.77 | $8.23 | $0.00 | $8.23 |
| Laboratory General Service 12231D1 | 21912E 597881 | $37.00 | $24.85 | $12.15 | $0.00 | $12.15 |

I've reviewed this claim and would like to begin with the eligibility survey.

< Back        Next >

Claims Opportunities

Save up to $247 — Anna by submitting your urgent care claim dated October 2, 2020 to AllInsure

You paid $453 recently in out-of-pocket expenses.

Orthopedic consult with Dr. Arun Bhatnagar on October 1, 2020

Did you pay $211.50 out of pocket for your visit with Dr. Bhatnagar on October 1, 2020?

☑ Yes

☐ No

< Back | Next >

Claims Opportunities

Save up to $247

Anna by submitting your urgent care claim dated October 2, 2020 to AllInsure

You paid $453 recently in out-of-pocket expenses.

Orthopedic consult with Dr. Arun Bhatnagar on October 1, 2020

Which of the following descript the related visit(s)

- ☑ Fracture/disclocation resulting in a surgury
- ☑ Hospital Admission
- ☑ Ground Ambulance
- ☐ Air Ambulance
- ☐ Fracture/disclocation not resulting in a surgury
- ☑ Other Injury

[ < Back ]  [ Next > ]

Claims Opportunities

Save up to $247
Anna by submitting your urgent care claim dated October 2, 2020 to AllInsure

You paid $453 recently in out-of-pocket expenses.

Orthopedic consult with Dr. Arun Bhatnagar on October 1, 2020

Who was injured during this recent accident?

- ✓ Just me
- ☐ My spouse and me
- ☐ My kids and me
- ☐ My spouse, kids, and me

< Back    Next >

MACHINE-LEARNING DRIVEN REAL-TIME DATA ANALYSIS

BACKGROUND

Submission of insurance claims can be a confusing and stressful process. The insured may be covered by multiple insurance policies that each provide coverage for various types of claims, such as but not limited to medical insurance, dental insurance, accident insurance, hospital indemnity insurance, and auto insurance. Each of these policies may cover a variety of different types of claims, and the insured may not have a complete understanding of the minutiae of the coverage provided by each of the policies or how to submit a claim for reimbursement. As a result, the insured may miss opportunities to have claims reimbursed that could have been reimbursed by one of the insurers. Hence, there is a need for improved systems and methods that provide a technical solution for solving the technical problem of automatically analyzing insurance claims and policy information to identify an insurer that is likely to cover the insurance claims to improve reimbursement rates for insurance claims.

SUMMARY

An example data processing system according to the disclosure may include a processor and a computer-readable medium storing executable instructions. The instructions when executed cause the processor to perform operations including obtaining electronic copies of a plurality of insurance policies associated with an insured user; analyzing the electronic copies of the plurality of insurance policies to generate policy coverage information for each of the insurance policies; obtaining an electronic copy of a plurality of insurance claims associated with the insured user; analyzing the electronic copy of the plurality of insurance claims to generate insurance claim information; providing the generated insurance claim information as an input to a first machine learning model; analyzing the insurance claim information using the first machine learning model to identify an occurrence of a first type of event and a first group of insurance claims associated with the first type of event, wherein the first machine learning model is trained to predict and output an occurrence of a type of event requiring medical treatment based on a group of insurance claims associated with the insured user; providing the indication of the occurrence of the first type of event and the first group of insurance claims output from the first machine learning model, the policy information, and an indication of the first as an input to a second machine learning model; analyzing the first group of insurance claims, the policy information, and the indication of the first type of event using a second machine learning model to obtain a prediction whether a respective insurance policy of the plurality of insurance policies will cover the first group of insurance claims by identifying one or more types of policies in the policy information that are likely to cover the first group of insurance claims and predicting that the respective policy is likely to cover the first group of insurance claims by comparing the first group of insurance claims to policy provisions of the respective policy; providing the respective insurance policy of the insurance policies which will cover the first group of insurance claims output by the second machine learning model to a user interface module; and causing a user interface to be presented on a display of the computing device associated with the insured user to guide the insured user through submitting the first group of insurance claims to an insurance provider associated with the respective insurance policy.

An example method implemented in a data processing system for insurance claims analysis and adjudication includes obtaining electronic copies of a plurality of insurance policies associated with an insured user; analyzing the electronic copies of the plurality of insurance policies to generate policy coverage information for each of the insurance policies; obtaining an electronic copy of a plurality of insurance claims associated with the insured user; analyzing the electronic copy of the plurality of insurance claims to generate insurance claim information; providing the generated insurance claim information as an input to a first machine learning model; analyzing the insurance claim information using the first machine learning model to identify an occurrence of a first type of event and a first group of insurance claims associated with the first type of event, wherein the first machine learning model is trained to predict and output an occurrence of a type of event requiring medical treatment based on a group of insurance claims associated with the insured user; providing the indication of the occurrence of the first type of event and the first group of insurance claims output from the first machine learning model, the policy information, and an indication of the first as an input to a second machine learning model; analyzing the first group of insurance claims, the policy information, and the indication of the first type of event using a second machine learning model to obtain a prediction whether a respective insurance policy of the plurality of insurance policies will cover the first group of insurance claims by identifying one or more types of policies in the policy information that are likely to cover the first group of insurance claims and predicting that the respective policy is likely to cover the first group of insurance claims by comparing the first group of insurance claims to policy provisions of the respective policy; providing the respective insurance policy of the insurance policies which will cover the first group of insurance claims output by the second machine learning model to a user interface module; and causing a user interface to be presented on a display of the computing device associated with the insured user to guide the insured user through submitting the first group of insurance claims to an insurance provider associated with the respective insurance policy.

An example computer-readable storage medium according to the disclosure on which are stored instructions which when executed cause a processor of a programmable device to perform operations of obtaining electronic copies of a plurality of insurance policies associated with an insured user; analyzing the electronic copies of the plurality of insurance policies to generate policy coverage information for each of the insurance policies; obtaining an electronic copy of a plurality of insurance claims associated with the insured user; analyzing the electronic copy of the plurality of insurance claims to generate insurance claim information; providing the generated insurance claim information as an input to a first machine learning model; analyzing the insurance claim information using the first machine learning model to identify an occurrence of a first type of event and a first group of insurance claims associated with the first type of event, wherein the first machine learning model is trained to predict and output an occurrence of a type of event requiring medical treatment based on a group of insurance claims associated with the insured user; providing the indication of the occurrence of the first type of event and the first group of insurance claims output from the first machine learning model, the policy information, and an indication of the first as an input to a second machine learning model; analyzing the first group of insurance claims, the policy information, and the indication of the first type of event using a second machine learning model to obtain a prediction whether a respective insurance policy of the plurality of insurance policies will cover the first group of insurance claims by identifying one or more types of policies in the policy information that are likely to cover the first group of insurance claims and predicting that the respective policy is likely to cover the first group of insurance claims by comparing the first group of insurance claims to policy provisions of the respective policy; providing the respective insurance policy of the insurance policies which will cover the first group of insurance claims output by the second machine learning model to a user interface module; and causing a user interface to be presented on a display of the computing device associated with the insured user to guide the insured user through submitting the first group of insurance claims to an insurance provider associated with the respective insurance policy.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The drawing figures depict one or more implementations in accord with the present teachings, by way of example only, not by way of limitation. In the figures, like reference numerals refer to the same or similar elements. Furthermore, it should be understood that the drawings are not necessarily to scale.

FIGS. 5A, 5B, 5C, 5D, 5E, 5F, 5G, and 5H show an example user interface for linking a CAAS account to an insurer account.

FIGS. 6A, 6B, 6C, 6D, 6E, and 6F show an example user interface for providing recommendations for submitting claims.

DETAILED DESCRIPTION

Figure 1:
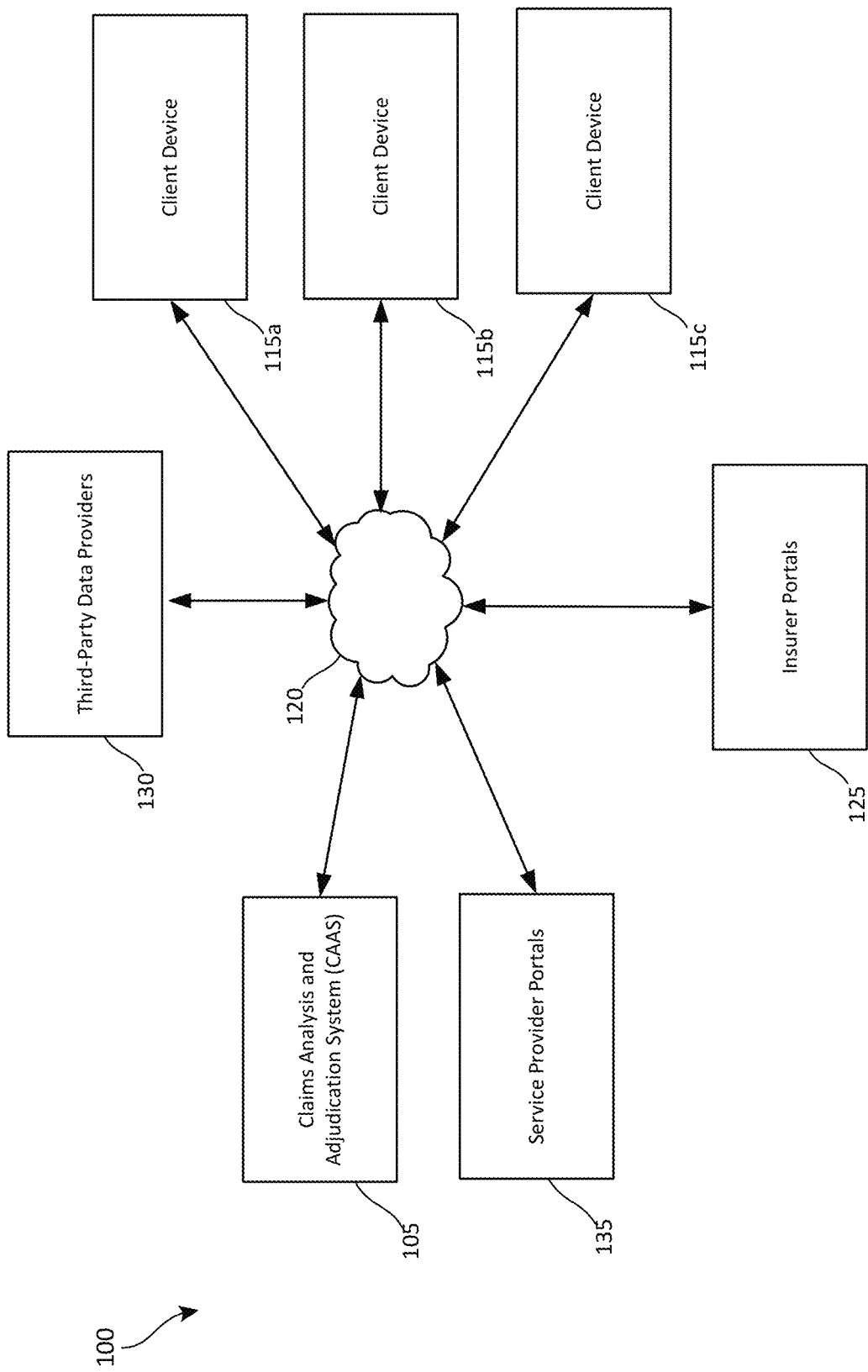
FIG. 1 is a diagram showing an example computing environment in which the techniques disclosed herein may be implemented.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Techniques are described herein for machine-learning driven insurance claims analysis and adjudication that provides a technical solution to the problem of determining whether an insurer associated with an insurance policy is likely to reimburse the insured for an insurance claim. The machine-learning model may be trained to analyze policy information for insurance policies associated with the insured, insurance claims information filed on behalf of the insured, and prescription information and output a prediction whether a particular insurer associated with one of the policies would pay one or more of the claims. An insured person may have multiple insurance policies that each have a complex list of the types of claims that the insurer may cover and the coverage limitations that provide the conditions under which the insurer may cover such claims. The insured person typically does not have a clear understanding of the myriad of coverage limitations associated with each of the insurance policies and may miss an opportunity to have a claim reimbursed by an insurer by submitting the claims to the wrong insurer or failing to submit a claim for which the insured person was entitled to coverage. The techniques provided herein may identify a policy likely to reimburse the user for the claim by analyzing the policy documents to obtain coverage information, including but not limited which types of claims are covered by each policy, the limits of coverage provided by each policy, other information that may be used to determine whether an insurer may cover a particular claim, or a combination thereof. The techniques described herein may also track the claims submitted by the insured over time, make a prediction that the claims are related to a particular type of event using machine learning model trained to analyze claims, and group the claims into groups of claims that are predicted to be associated with particular events. Examples of the types of events that may be identified include, but are not limited to, automobile accidents, sports injuries, illness-related events, or other type of events that the machine learning model may be trained to recognize that may be related to a particular type of claim or claims. The groups of claims may then be analyzed, and predictions generated that a particular insurer is likely to cover a claim or a group of claims. Where a definitive prediction cannot be made whether a particular insurer may reimburse the insured for a particular claim or set of claims, a set of dynamic questions may be presented to the user to disambiguate whether a particular insurer may reimburse a particular claim or group of claims or to disambiguate between multiple insurers that may reimburse the claim or group of claims. A technical benefit of this approach is that the system may recognize patterns in insurance claims over time and provide recommendations to the insured for how to get these claims reimbursed by insurers. As a result, the reimbursement rate for insurance claims may be significantly improved compared to manual processing of the claims by the insured. Another technical benefit provided by the techniques described herein is that the machine learning models may be trained using data that has been parsed and standardized into a standard schema. Furthermore, the data to be analyzed by the machine learning models may also be parsed and standardized. As a result, the machine learning models are receiving data in a format that utilizes descriptions that are consistent with the training data used to train the models. Consequently, the predictions provided by the models may be significantly improved in comparison to models which are not trained using such a technique. The techniques provided herein also provide for substantially real-time analysis of claims information from a combination of data sources that may also significantly improve the predictions provided by the machine learning models and provide the user with recommendations that are more likely to allow the user to optimize their usage of their benefits by using accurate and update date information. These and other technical benefits of the techniques disclosed herein will be evident from the discussion of the example implementations that follow.

The techniques provided herein satisfy a long-felt need for improving insurance claims analysis and adjudication to provide insured with a means for optimizing the use of their benefits. Furthermore, the solution provided to this problem is rooted in computer technology to overcome a problem arising in realm of computer systems for providing substantially real-time analysis and adjudication of claims in a manner that accurately predicts which insurers are likely to cover a particular group of claims.

FIG. 1 is a diagram showing an example computing environment 100 in which the techniques disclosed herein for insurance claims analysis and adjudication may be implemented. The computing environment 100 may include a claims analysis and adjudication system (CAAS) 105, one or more client devices 115, one or more insurer portals 125, one or more provider portals 135, and one or more third-party data providers 130. The example implementations shown in FIG. 1 includes three client devices 115a, 115b, and 115c, but the techniques described herein may be used with a different number of client devices 115. The client devices 115a, 115b, and 115c may communicate with the CAAS 105, the insurer portals 125, provider portals 135, and/or the third-party data providers via the network 120. The CAAS 105 may also communicate with the client devices 115a, 115b, and 115c, the insurer portals 125, the provider portals 135, and/or the third-party data providers 130 via the network 120. The network 120 may include one or more wired and/or wireless public networks, private networks, or a combination thereof. The network 120 may be implemented at least in part by the Internet.

The client devices 115a, 115b, and 115c may be used by an insured to access the services provided by the CAAS 105, insurance information from the insurer portals 125, and/or information from the third-party data providers 130. The client devices 115a, 115b, and 115c are each a computing device that may be implemented as a portable electronic device, such as a mobile phone, a tablet computer, a laptop computer, a portable digital assistant device, a portable game console, and/or other such devices. The client devices 115a, 115b, and 115c may also be implemented in computing devices having other form factors, such as a desktop computer, vehicle onboard computing system, a kiosk, a point-of-sale system, a video game console, and/or other types of computing devices. While the example implementation illustrated in FIG. 1 includes three client devices, other implementations may include a different number of client devices. The client devices 115a, 115b, and 115c may be used to access the applications and/or services provided by the insurer portals 125 and/or the CAAS 105.

The insurer portals 125 may be provided by insurance providers to as a means for insured user to access their policy information, make policy payments, obtain new policies, to submit claims on existing policies, and/or perform other actions related to the managing the insured's insurance. An insured user may have policies with multiple insurers, and thus, may have to access multiple insurer portals 125 to obtain information related to each of their insurance policies. Consequently, the insured user must learn to navigate multiple insurance portals that may have significantly different layouts in order to access their policy information, submit claims and/or check on claim status, or perform other actions related to their policy.

The service provider portals 135 may provide a means for doctors, dentists, optometrists, and/or other medical professionals to submit claims to the insurers on behalf of an insured user. The service provider portals 135 may provide means for the providers to check on the status of a claim with an insurer. The service provider portals 135 may also permit the providers to amend and/or resubmit claims.

The CAAS 105 provides a cloud-based or network-based portal for accessing the services provided by the CAAS 105. The CAAS 105 may be configured to provide secure and delegated access to insurance claims for insured users. The CAAS 105 may implement a claims application programming interface (API) infrastructure that allows the insured users to access their insurance claims data and to provide various services such as claims analysis and adjudication services, guidance for optimizing prescription benefits, guidance for optimizing medical spending account (MSA) usage, guidance for proactive benefits engagement, services which may assist the insured in selecting a bundle of insurance products that satisfies the insured requirements, and/or other services related to optimizing the insurance coverage and utilization by the insured. Among the services provided by the CAAS 105, the CAAS 105 provides substantially real-time claims analysis and adjudication. The CAAS 105 may utilize a machine-learning model or models trained to analyze the claims to guide the user through submitting the claims to the appropriate insurer and to provide other advice for optimizing the use of the coverage provided to the user by their policies. The CAAS 105 may also respond to changes in the demographic data of the user and may provide a proposed bundle of insurance policies that meet the changing needs of the user. The example implementations which follow provide additional details describing these and other features of the CAAS 105.

The CAAS 105 may be configured to collect policy and claims information for users from the insurer portals 125, to analyze the information included in the policy information to obtain coverage information. The coverage information may include which types of claims are covered by each policy, the limits of coverage provided by each policy, other information that may be used to determine whether an insurer may cover a particular claim, or a combination thereof. The CAAS 105 may be configured to implement a set of secure and authenticated pipelines that are configured to allow members to link to their accounts with their insurance providers to obtain plan information, claims information, or both. The CAAS 105 may provide a user interface that provides a list of supported insurers. The user may select an insurer from the list of supported insurers and the user interface guides the user through setting up the connection with the user's account with that insurer. The user may securely provide authentication details that permit the CAAS 105 to securely access the policy information and/or claims information provided through the insurer portals 125. The CAAS 105 may access the policy information, claims information, or both, analyze this information, and convert the information to a unified and standardized schema for this information. The standardized information may be stored by the CAAS 105 to provide various services to user, which will be discussed in greater detail with respect to the example implementation of the CAAS 105 shown in FIGS. 2 and 3.

The third-party data sources 130 are additional data sources that may be accessed by the CAAS 105 to obtain additional information for a user. The CAAS 105 may be configured to use the third-party data to supplement information collected from the user. The CAAS 105 may be configured to collect at least some demographic information from the user by presenting a set of dynamically generated questions to the user. The questions presented to the user may be dynamically selected based at least in part on the user's responses to previous questions, to information included in the third-party data, or a combination thereof. The third-party information and/or information that may be collected from the user may include, but is not limited to, the user's medical history, past insurance consumption, the user's financial profile (debts, assets, liabilities), credit history, family information, psychographics, interests, occupation, salary, physical activity, and other information that may be used by the CAAS 105 to facilitate providing insurance plan recommendations to the user. The CAAS 105 may query the third-party data sources 130 for information and may reformat the data into a standard schema used by the CAAS 130 for storing and analyzing the data. The CAAS 105 may also be configured to disambiguate the data received from the third-party data sources where the data includes information associated with multiple people who may or may not be the user. Additional details of data disambiguation are provided in the examples which follow.

Figure 5A:
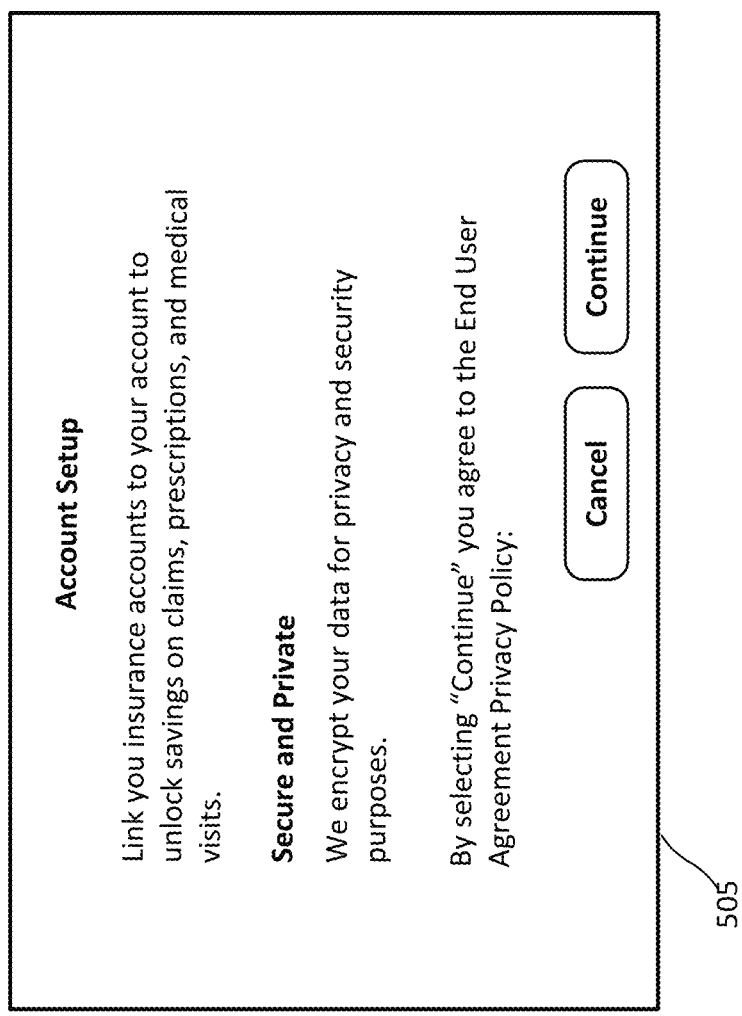
Figure 5B:
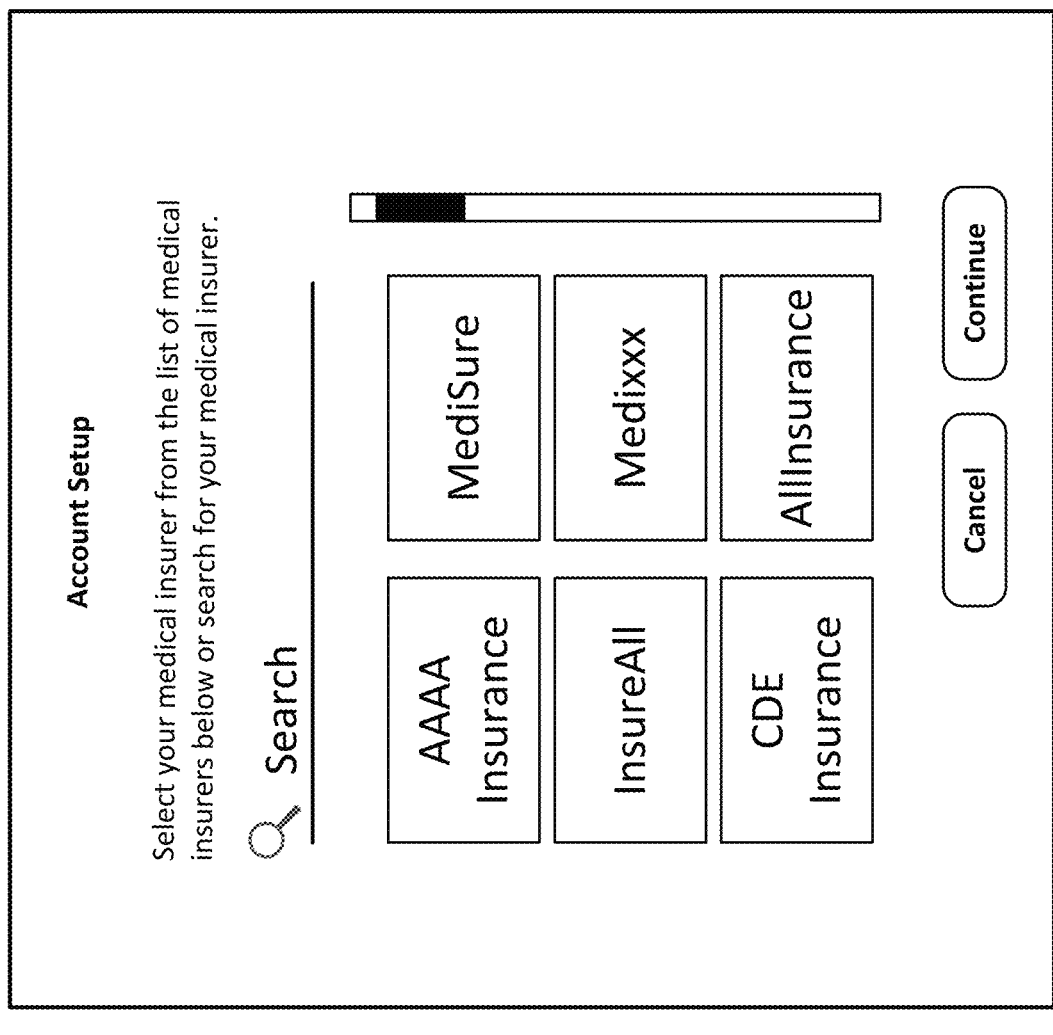
Figure 5C:
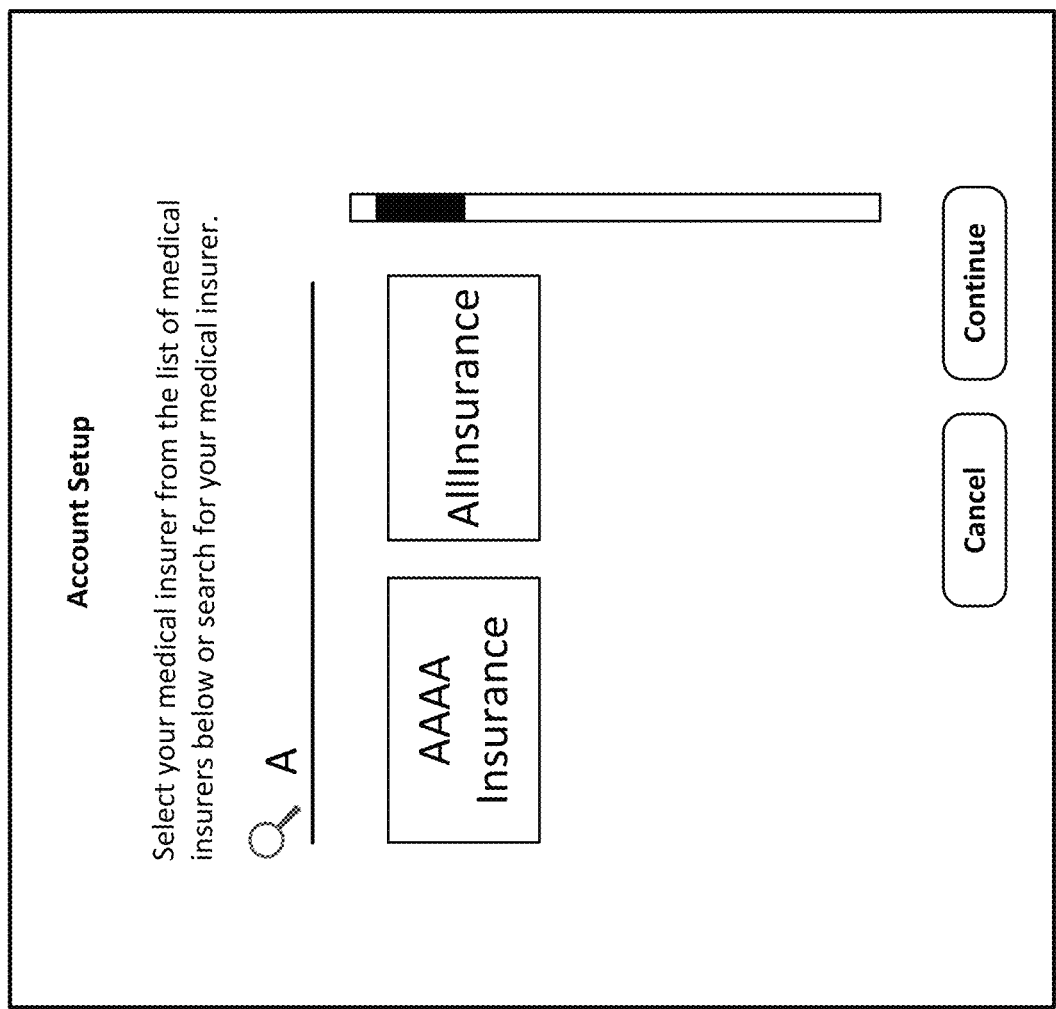
Figure 5D:
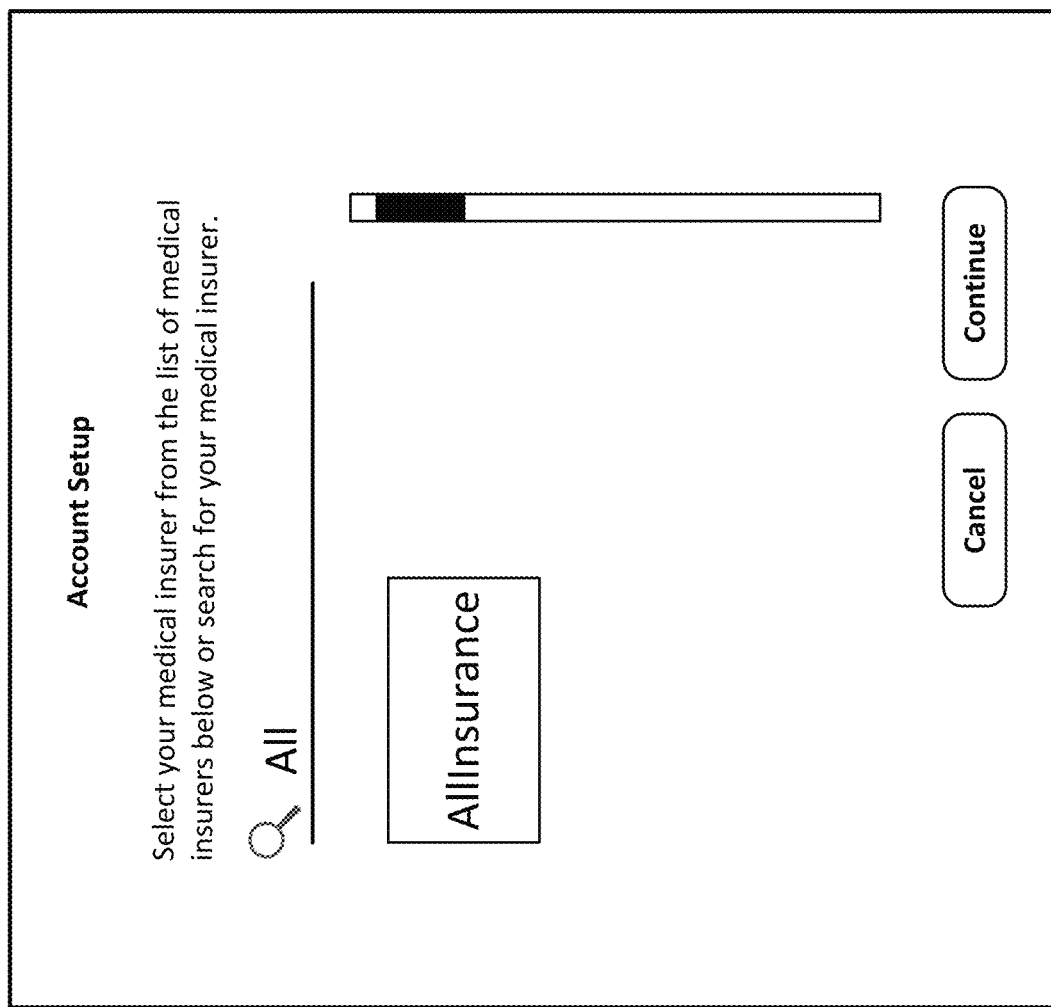

FIGS. 5A-5H show an example of the CAAS 105 guiding a user through the process of linking the user's account with an insurer to the user's CAAS account so that the CAAS 105 may obtain policy and claim information associated with the user from the insurer portal 125. FIG. 5A shows a user interface 505 for starting the setup process that presents information to the user regarding the account setup process. The user may click on the "Continue" button to cause the CAAS 105 to advance to the user interface 510 shown in FIG. 5B. The user interface 510 provides a list of insurers to which the CAAS 105 has been configured to permit the user to link the CAAS account to the user's account on the insurer's system. The user may select the icon associated with a particular insurer or type the name of the insurer in the search field. FIGS. 5C and 5D show that the list of insurers may be narrowed dynamically as the user types in the search field. FIG. 5E shows an example of a user interface 515 that may be displayed for the selected insurer. The user may provide their authentication credentials for the insurer portal and click submit. The CAAS 105 will attempt to access the insurer portal 125 using the provided authentication criteria. FIGS. 5F and 5G show an example two-factor authentication user interface 520 that may be used to further secure access to the user account on the insurer portal 125. Once the user has been authenticated with the insurer's portal, the user interface 525 may be displayed to confirm that the accounts have been linked. The CAAS 105 may then access claims information, policy information, and/or other information from the insurer portal 125.

Figure 2:
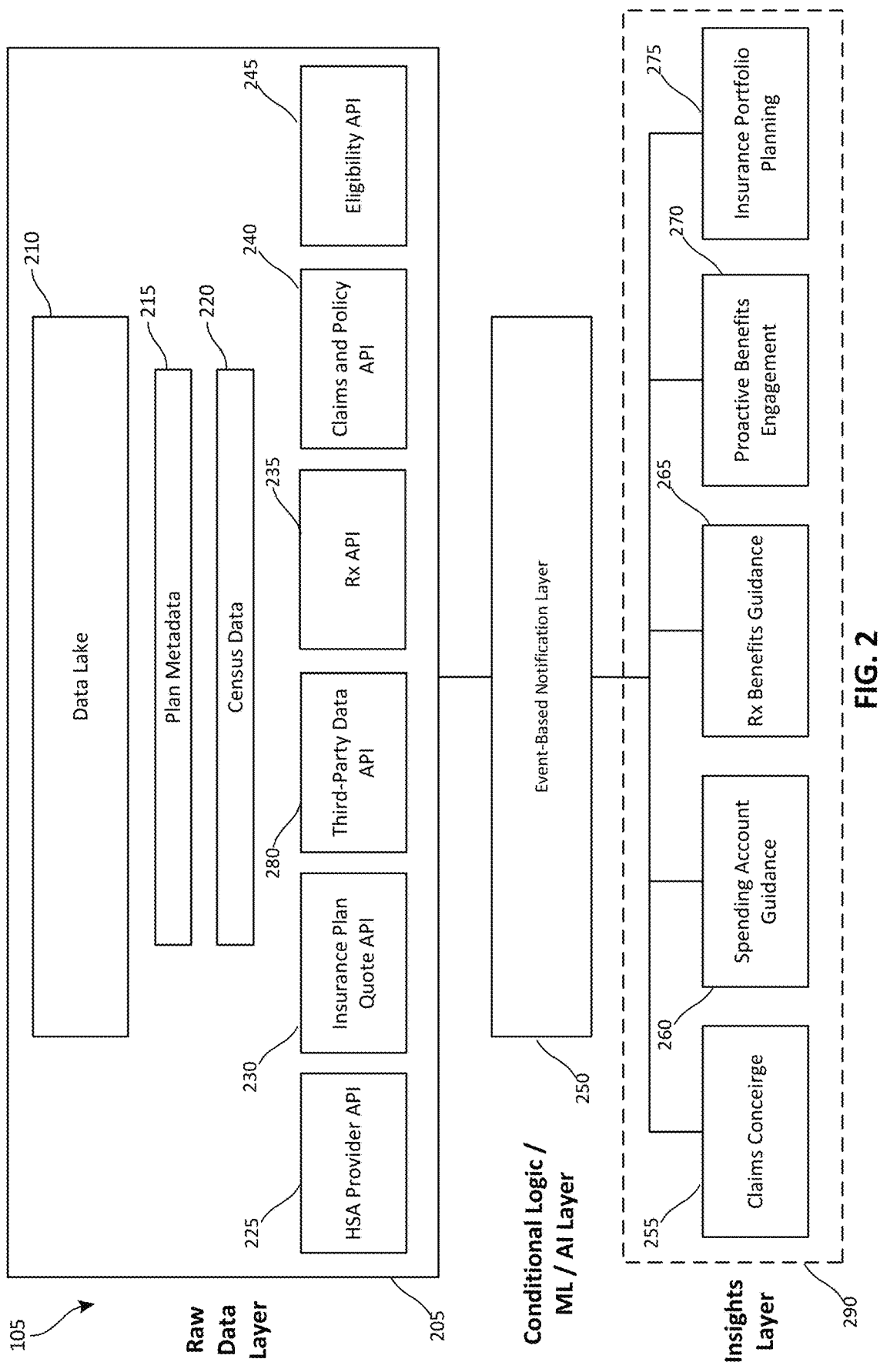
FIG. 2 is a diagram of an example architecture that may be used, at least in part, to implement the claims analysis and adjudication system (CAAS) shown in FIG. 1.

FIG. 2 is a diagram of an example implementation of a CAAS 105 shown in FIG. 1 that shows additional elements of the CAAS 105. The CAAS 105 shown in FIG. 2 includes three layers: (1) a raw data layer 205, (2) an event-based notification layer 250, and (3) an insights layer 290. The raw data layer 205 may be configured to obtain insurance data for users from various data sources, to convert this data to a unified and standardized schema, and to store the user data for analysis by the event-based notification layer 250 and/or the insights layer 290 to provide various insurance-related services to the users. Additional details of the functions of each of these layers will be described in greater detail in the examples which follow. In some implementations, the functions of each of these layers may be grouped together into a different number of functional layers. Furthermore, the functionality of each of the layers may be implemented on separate servers in some implementations, and the servers may be communicably coupled over public and/or private network connections to permit the various components of the CAAS 105 to exchange and analyze data.

The raw data layer 205 may include a data lake 210, a plan metadata data store 215, a census data datastore 220, a health savings account (HSA) provider API 225, an insurance plan quote API 230, a prescription API 235, a claims and policy API 240, an eligibility API 245, and a third-party data API 280. The APIs provide pipelines for obtaining data that that the CAAS 105 may use to provide various insurance-related services. User data may be protected by secure and authenticated pipelines when accessing sensitive data. The CAAS 105 may guide a user through setting up authentication with the external data sources to allow the CAAS 105 to securely access the user data.

Figure 3:
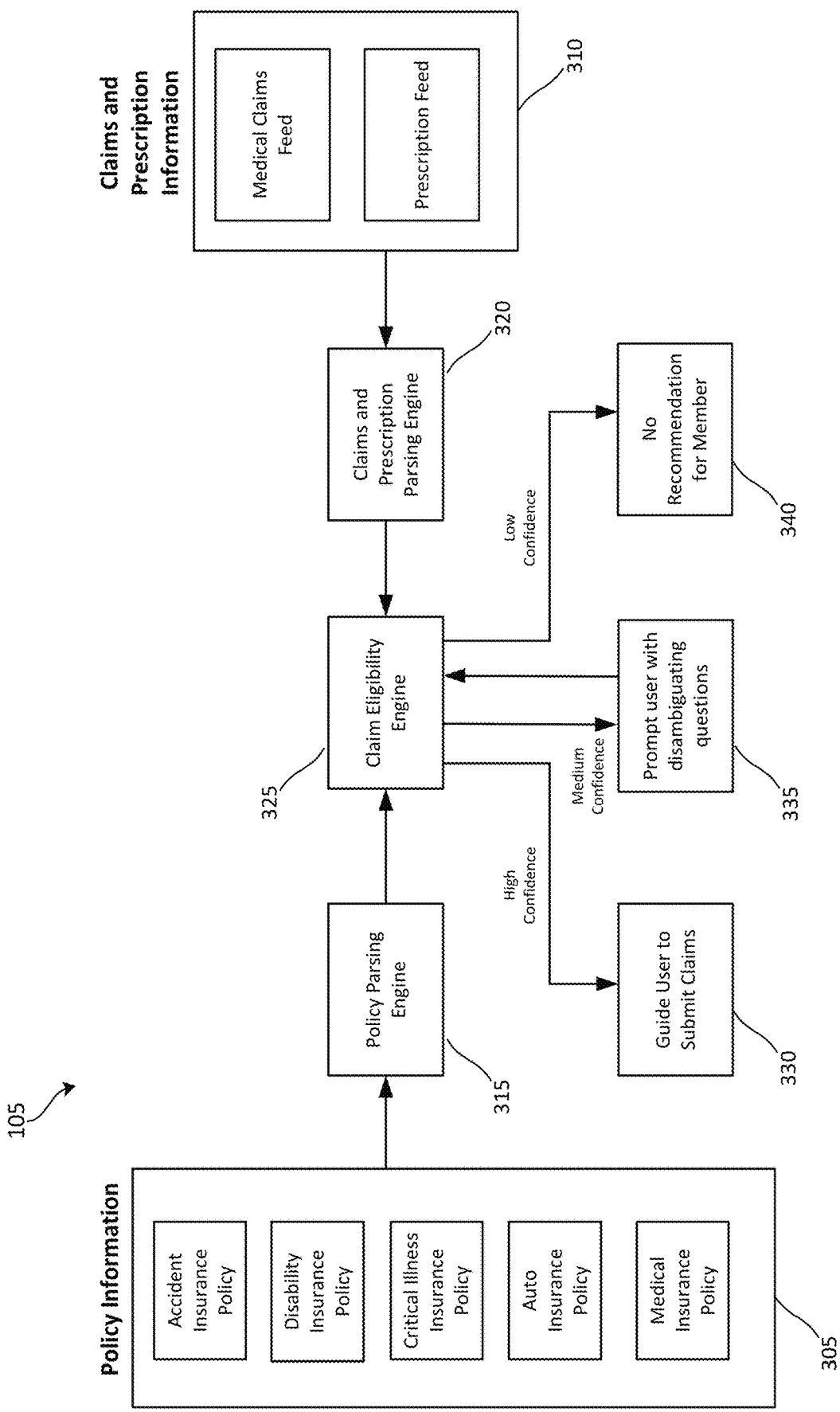
FIG. 3 is a diagram of an example architecture that shows additional details of a CAAS which may be used to implement the CAAS shown in FIGS. 1 and 2.

The data lake 210 may be used to store raw user data, raw claims data, and raw policy data that has been obtained from one or more external data sources, such as but not limited to the insurer portals 125 and the third-party data providers 130. Raw data, as used herein, refers to an original data format in which the data was obtained from the external data source. The format of the raw data may depend on the type of data and the external data source from which the data was obtained. The raw data may be retained in the data lake 210, and the raw data 210 may be processed into a standard schema by one or more parsing engines of the CAAS 205. The standard schema defines a set of logical data structures that may be used by the CAAS 205 storing and analyzing data. FIG. 3, which will be discussed in greater detail below, includes two parsing engines, a policy parsing engine 315 and a claims and prescription parsing engine 320 for parsing data. While the example shown in FIG. 3 includes two separate parsing engines, the functionality of the parsing engines may be combined into a single parsing engine or into more than the two parsing engines shown in FIG. 3. The standardized policy data may be stored in the plan metadata 215.

The policy data may include coverage information, including but not limited to the types of claims are covered by each policy, the limits of coverage provided by each policy, other information that may be used to determine whether an insurer may cover a particular claim for a user. The census data 220 may include demographic information that is collected from the user by the CAAS 205, information about the user obtained from third-party data sources 130, information obtained from the insurer portals 125, and/or other information about the users that may be used by the CAAS 205 to provide recommendations to the user regarding insurance-related issues. The user-related data obtained from these various sources may be formatted into a standard schema by one or more parsing engines of the CAAS 205 and stored in the census data 220.

The raw data layer 205 shown in FIG. 2 includes six API units configured to implemented APIs for accessing data from various sources. Some implementations of the raw data layer 205 of the CAAS 105 may include a different number of APIs for accessing data from the various data sources. The types of data sources accessed and processed by the raw data layer may depend at least in part on the functionality provided by the insights layer 290 discussed in greater detail in the examples which follow.

The claims and policy API 240 is configured to obtain policy information and/or insurance claims information from insurers via the insurer portals 125. As discussed in the preceding examples, the CAAS 205 may be configured to provider a user interface that guides the user through linking their account with the CAAS 205 to their accounts with their insurers. The claims and policy API 240 may be configured to retrieve policy information and/or claims information from each insurer and store the raw data in the data lake 210. The insurance policy information may be converted to the standard schema by the policy parsing engine 315 and the claims information may be converted to a standard schema by the claims and prescriptions parsing engine 320 shown in FIG. 3.

The policy information for users may be kept up to date in substantially real-time. The claims and policy API 240 may be configured to periodically check for updates to the policy information for users. The claims and policy API 240 may also check for updates to the policy information for the user in response to a request from the event-based notification layer 250 or the insights layer 290. In some implementations, the claims and policy API 240 may receive updates to the claims information and/or the policy information from the insurer in response to the changes or renewal of a policy or in response to claims being submitted to the insurer for reimbursement.

The HSA provider API 225 may be configured to obtain information from one or more HSA providers. The HSA provider API 225 can obtain information associated with the HSA account of a user, such as but not limited to the current balance, historical reimbursement information for claims reimbursed by the HSA account, and/or other information associated with the usage of the HSA account. The HSA account information may be used by the CAAS 205 to build a historical model of the number and types of claims submitted for reimbursement by the user and to make predictions for recommended future funding of the HSA based on the historical usage. The HSA account information may also be considered by the CAAS 205 when analyzing the insurance coverage of the user and for recommending coverage that accommodates the needs of the user.

The prescription API 235 may be configured to obtain prescription price information from a pharmacy benefits manager (PBM). Information regarding the prescriptions that a user has been prescribed may be obtained directly from the user and/or determined based on the claims information obtained from the insurance providers via the claims and policy API 240. The prescription price information may be utilized by the prescription benefits guidance unit 265.

The insurance plan quote API 230 may be configured to obtain quotes for insurance coverage from insurers that may be used by the CAAS 205 to create a comprehensive bundle of insurance policies for a user based at least in part on predicted insurance consumption by the user. The insurance plan quote API 230 may be configured to submit requests for quotes to insurers for medical insurance, dental insurance, accident insurance, hospital indemnity insurance, auto insurance, and/or other types of insurance. The insurance portfolio planning unit 275 may use the quote information to build a comprehensive insurance plan for the user that is based on the needs of the user. The insurance portfolio planning unit 275 may determine the needs of the user based on user data that includes, but is not limited to, the user's medical history, past insurance consumption, the user's financial profile (debts, assets, liabilities), family information, psychographics, interests, occupation, salary, physical activity, and/or other information that may be used to infer the needs of the user.

The eligibility API 245 may be configured to verify enrollment of a user with an insurer. The API 245 may be used to determine whether the user is covered by a particular policy and whether the user is eligible for certain types of claims to be reimbursed by the insurer. The eligibility information may be utilized by the CAAS 205 to determine whether a particular claim or type of claims may be covered by a particular insurer. The eligibility information may be accessed substantially in real-time so that recommendations provided by the CAAS 205 are based on current enrollment status of the user.

The third-party data API 280 may be configured to submit queries for third-party data to the third-party data provider 130. The third-party data sources may include but are not limited to sources of medical history data, financial profile information, credit history information, marital status information and/or family information, occupation, salary, and/or other information that may be used by the CAAS 105 to provide various recommendations to the user. The third-party data API 280 may be used by the various components of the CAS 105 to query the various data sources for third party data.

The event-based notification layer 250 may utilize conditional logic, machine learning models, and/or artificial intelligence systems for analyzing the data obtained and/or generated by the raw data layer 205. The event-based notification layer 250 may be configured to analyze the data from the raw data layer 205 to support the functionality of the services provided by the insights layer 290. The event-based notification layer 250 may utilize one or more machine learning models to analyze the data maintained by the raw data layer 205. The event-based notification layer 250 may implement elements of the bundle recommendation engine 325 shown in FIGS. 3 and 4.

The insights layer 290 may provide various services to the user based on the analysis of the data by the event-based notification layer 250. The insights layer 290 includes a claims concierge unit 255, a spending account guidance unit 260, a prescription benefits guidance unit 265, a proactive benefits engagement 270, and an insurance portfolio planning unit 275.

The claims concierge unit 255 may be configured to analyze claims data and to provide recommendations to the user for submitting the claims to an insurer. The claims concierge unit 255 may be configured to automatically analyze claims data to identify claims that may be paid by an insurer. The claims concierge unit 255 may also provide recommendations in response to a request from a user to analyze one or more pending insurance claims. Additional features of the claims concierge unit 255 are shown in the examples which follow.

The spending account guidance unit 260 may provide guidance to the user for optimizing the funding of the MSA based on prior health plan consumption and utilizing the MSA funds to reimburse medical claims costs. The prescription benefits guidance unit 265 may provide guidance to the user for providing prescription price guidance to the user including prices at which prescriptions medications are being offered at pharmacies located near the user.

The proactive benefits engagement unit 270 may provide recommendations for the user for optimizing the usage of their benefits. The proactive benefits engagement unit 270 may be configured to provide meaningful and actionable notifications to encourage users to engage with the benefits provided by their insurance policies. The proactive benefits engagement unit 270 may consider the personal finances of the user when making recommendations to the user regarding the usage of the user's benefits.

The insurance portfolio planning unit 275 may provide recommendations to the user for building insurance bundles that consider the user's demographics, risk aversion of the user, and the needs of the user.

FIG. 3 is a diagram that shows an example implementation of a claim eligibility engine 325 that may be implemented by the CAAS 105. The implementation shown in FIG. 3 may be configured to map a user's insurance claims to the user's insurance policies. The CAAS 105 may utilize one or more machine-learning models trained to analyze the insurance claims to guide the user to submitting the claims to the appropriate insurer.

The policy information 305 may include multiple insurance policies, such as but not limited to medical insurance policies, dental insurance policies, accident insurance policies, disability insurance policies, critical illness insurance policies, auto insurance policies, and/or other types of insurance policies. The policy information 305 may be obtained by the claims and policy API 240 of the raw data layer 205 shown in FIG. 2. Electronic copies of the policies may be obtained from the insurers in a Portable Document Format (PDF) or another electronic format supported by each insurer. Insurers may support different electronic file formats and the layout of the policy information provided by each insurer may vary. The policy information obtained from the insurers may be stored in the data lake 210 of the raw data layer 205. The policy parsing engine 315 may be configured to analyze the raw policy data obtained from the insurers and to convert the policy information to a standard schema. The standardized information may be stored in the plan metadata 215. The plan metadata may include coverage information, policy limits, deductible information, and/or other information that may be used by the CAAS 105 to determine whether a particular insurer may reimburse the policy holder for a particular type of claim or claims.

The policy parsing engine 315 may be configured to use fuzzy matching techniques to map policy coverage information extracted from the insurance policies to standardized coverage information. Insurers may use slightly different language to describe the coverage provided. The policy parsing engine 315 may be configured to map the policy coverage information with a set of standardized insurance coverage descriptions maintained by the CAAS 105. The standardized insurance coverage descriptions may include descriptions of types of coverage that may be offered by insurers. The policy parsing engine 315 may be configured to perform a probabilistic data match on the coverage information provided in an insurance policy with the standardized coverage descriptions. The policy parsing engine 315 may be configured to select a standardized description that is associated with the highest probability of being a match with the policy coverage description. The matching standardized description may be stored in with the policy information in the plan metadata 215 and may be used by the claim eligibility engine 325 to determine whether the user has a policy that is likely to cover the claim.

Mapping the policy coverage information to standard descriptions may provide a significant technical benefit by improving the predictions that are provided by the machine learning models used by the claim eligibility engine 325. The machine learning models may be trained using training data that includes the same standard insurance coverage descriptions that will be used by the claim eligibility engine 325 to determine whether a particular claim is likely to be covered by a user's insurance policy. Thus, the machine learning models may be presented policy coverage data for analysis that utilizes descriptions consistent with the coverage descriptions included in the training data used to train the model.

The claims and prescription information 310 may include substantially real-time information from a medical claims feed and prescription feed. The medical claims information represents insurance claims that the user has submitted or has had submitted on their behalf for reimbursement. The prescription information represents prescriptions that have been prescribed to the user and may be submitted for reimbursement to an insurer. The claims and/or prescription information may be obtained by the claims and policy API 240 shown in FIG. 2 and the data stored in the data lake 210. The claims and prescription information obtained from each of the insurers may be in different electronic formats and/or layouts. The claims and prescription information may be processed by the claims and parsing engine 320 to convert the claims and prescription information into the standard schema utilized by the CAAS 105. The claims and prescription information in the standardized schema may be stored with the plan metadata 215.

The claims and prescription parsing engine 320 may be configured to use fuzzy matching techniques to map the claims and prescription information 310 to standardized claims and prescription descriptions before the claims and prescription information is analyzed by the claim eligibility engine 325. Medical providers may use inconsistent language to describe the procedures performed. One medical provider may describe the same procedure in a slightly different way than another provider. Such inconsistencies in the description of the procedures performed can make determining whether a particular policy covers a particular claim or prescription. The set of standardized claim and prescription descriptions may provide a consistent set of descriptions that may be associated with claims and prescriptions. The claims and prescription parsing engine 320 may be configured to perform a probabilistic data match on the claims and prescription information 310 with the standardized claim and prescription descriptions. The claims and prescription parsing engine 320 may be configured to select a standardized description that is associated with the highest probability of being a match with the description of the procedure performed and/or other information included in the claim and/or prescriptions submitted to the insurer on behalf of a user.

The standardized description matched with a claim may be stored with the claim information in the plan metadata 215 associated with the claim. The standardized description may also be used by the claim eligibility engine 325 to determine whether the user has a policy that is likely to cover the claim. Mapping the claims and prescription information to standard descriptions provides the technical benefit of improving the predictions that are provided by the machine learning models used by the claim eligibility engine 325. The machine learning models may be trained using training data that includes the same standard claim and/or prescription descriptions that will be used by the claim eligibility engine 325 to determine whether a particular claim or prescription is likely to be covered by a user's insurance policy. Thus, the machine learning models are presented claims and prescription descriptions for analysis that utilizes descriptions consistent with the claims and prescription descriptions included in the training data used to train the model.

If the probability of the standardized description matching a particular claim is less than a predetermined threshold, the claims and prescription parsing engine 320 may flag the claim for additional processing. The user may be prompted to provide additional information that may be used to help disambiguate the claim and/or to request that a different description for the claim be provided. Standardizing the descriptions of the claims may increase the likelihood that the claim eligibility engine 325 may find a matching insurance policy that may cover the claim.

The standardized policy coverage information and the standardized claims and prescription information may be provided to the claim eligibility engine 325 for analysis. The claims eligibility engine may be configured to track multiple insurance claims over a period of time and make predictions that the claims are related to a particular event and grouping the claims accordingly. The claim eligibility engine 325 may use one or more machine learning models trained to group the insurance claim by event type. For example, the machine learning models may be configured to group the insurance claims by an event type, such as but not limited automobile accidents, sports injuries, illness-related events, or other type of events that the machine learning model may be trained to recognize that may be related to a particular type of claim or claims. The machine learning model or models may generate a prediction that groups of insurance claims are associated with a particular type of event. The claim eligibility engine 325 may be configured to analyze the groups of insurance claims with one or more machine learning models configured to generate a prediction whether a particular insurer for which the user has a policy is likely to cover a particular claim or group of claims.

The machine learning model or models may associate a confidence level with the predictions whether a particular insurer may cover a claim or group of claims, and the claim eligibility engine 325 may perform different actions in response to the confidence levels associated with the predictions. In response to the claim eligibility engine 325 having a low confidence in the prediction, the claims eligibility engine may provide an indication that no recommendation may be made for the member in operation 340. In response to the claim eligibility engine 325 having a medium confidence level, the claim eligibility engine 325 may be configured to present dynamically generated questions to the user in operation 335. The responses to the dynamically generated questions may be used to disambiguate whether a particular insurer may cover a particular claim or group of claims and/or to disambiguate between insurers to determine whether one insurer is more likely to cover the claim or group of claims. In response to the claim eligibility engine 325 having a high confidence level, the claim eligibility engine 325 may be configured to guide the user to submit the claim or group of claims to the insurer predicted to cover the claims in operation 330. The low, medium, and high confidence levels may be determined by determining whether the confidence level associated with a prediction with a particular range of confidence levels. These ranges may be configurable by an administrator of a system to configure how the claim eligibility engine 325 handles the predictions made by the machine learning model or model used to predict whether a particular insurer may cover a claim or set of claims.

Figure 4:
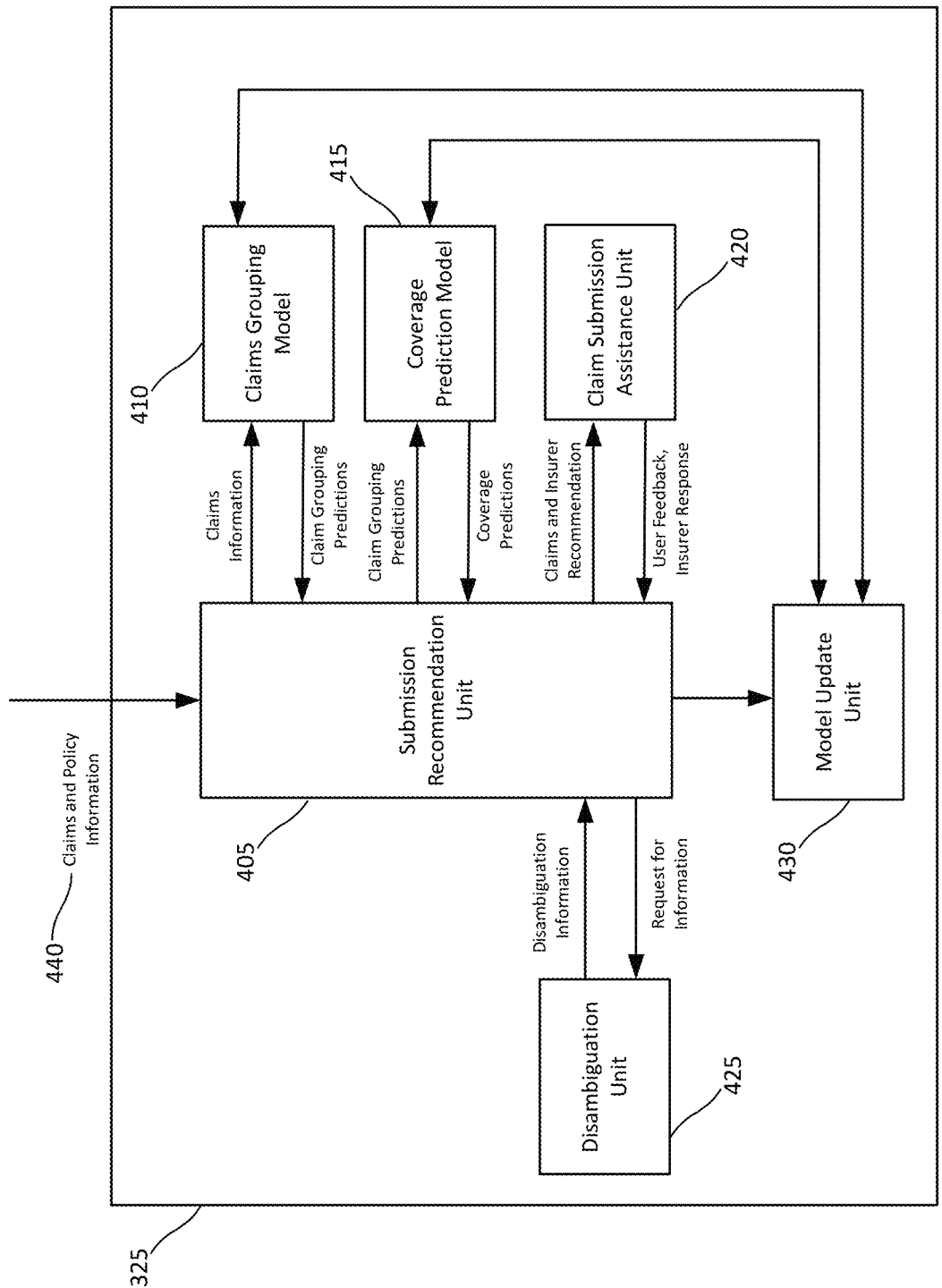
FIG. 4 is a diagram of an example architecture that shows additional details of the CAAS that may be used to implement the CAAS shown in FIGS. 1-3.

FIG. 4 is a diagram showing an example implementation of the claim eligibility engine 325. The claim eligibility engine 325 may include a submission recommendation unit 405, a claim grouping machine learning model 410, a coverage prediction model 415, a disambiguation unit 425, a claim submission assistance unit 420, and a model update unit 430. The claim eligibility engine 325 may analyze insurance claims and policy information and present recommendations to the user recommending a particular insurer to which the claims may be submitted. The recommendations may be generated on demand in response to a request from the user, in response to the CAAS 105 detecting new claims have been submitted for the user, in response to receiving a notification that one or more claims have been rejected by an insurer, and/or in response to other events which may trigger the CAAS 105 to analyze the pending claims for the user. For example, the CAAS 105 may receive an Explanation of Benefits (EOB) from an insurer that indicates that the insurer did not cover one or more claims and/or did not fully cover one or more claims. Claims that have been rejected by an insurer may have been rejected for various reasons, including but not limited to the user not being eligible for coverage of the claims under their policy, the user having reached their policy limits for that type of claim, or other reasons. Claims may only be paid in part by an insurer due to coverage limitations, insurance copays, or other reasons. The CAAS 105 may identify another insurer that may pay the claims and guide the user through submitting the claims to the other insurer.

The submissions recommendation unit may be configured to obtain claims and policy information 440 to be analyzed to predict an insurer that may cover the claims. The claims and policy information 440 include the standardized policy coverage information output by the policy parsing engine 315. The claims and policy information 440 may also include the claims and prescription information into the standard schema output by the claims and parsing engine 320.

The submission recommendation unit 405 may first analyze the claims and/or prescription information to group the claims into groups of claims predicted to be associated with a particular type of event. Claims associated with various types of events may be identified, such as but not limited to automobile accidents, sports injuries, illness-related events, or other type of events for which groups of certain types of claims may typically be associated. The submission recommendation unit 405 may be configured to provide the claims information to the claims grouping model 410 to obtain predictions as to logical groupings of the claims. The claims grouping model 410 may be one or more machine learning models which have been trained to recognize patterns in insurance claims and group the insurance claims according to these events. The insurance claims associated with a particular event may be submitted together or over a period of time. In an example to illustrate this concept, a user who experienced a sports-related injury may submit claims for emergency services, prescriptions, physical therapy, and/or other treatments or services related to the injury. Claims may be submitted for emergency services provided at the time the injury occurred, while other claims may be submitted for the physical therapy and/or other treatments that follow the initial treatment by emergency services.

The claims grouping model 410 may be trained to recognize a pattern in the insurance claims over time associated with such an injury and to group the claims as being related to a sport injury. In another example, a user who experienced an automobile accident may have claims related to emergency services and hospitalization as well as claims for damage to their automobile. These examples illustrate a couple of possible patterns in claims that the model may recognize but do not limit the model to recognizing these specific patterns.

The claims grouping model 410 may initially be trained using training data that has been hand labeled to associate certain types of claims with certain types of events. The training data may also represent patterns in the insurance claims. The training of the claims grouping model 410 may be further refined by providing feedback on predictions generated by the claims grouping model 410. In some implementations, the claim eligibility engine 325 may include more than one claims grouping model 410, and a prediction from one of the models having a highest confidence rating associated with the prediction.

The submission recommendation unit 405 may be configured to provide the claims grouping predictions from the claim groups information and an indication of the event type predicted by the claims grouping model 410 and policy information to the coverage prediction model 415. The coverage prediction model 415 may be trained to analyze the groups of claims and policy information to provide a prediction as to which insurer may cover the claims. The coverage prediction model 415 may be initially trained using hand-labeled training data that associates certain types of claims with certain insurance policy provisions. The coverage predication model 415 may identify policies that are likely to cover the claim or group of claims based on the event type predicted by the claims grouping model 410. Certain types of events may be covered by a particular type or types of policy. For example, medical claims for injuries related to an automobile crash may be covered by an automobile insurance policy and/or by a medical insurance policies. Other types of events may be associated with other types of claims that are likely to be covered by other types of policies. The coverage prediction model 415 may be configured to identify the types of policies that are likely to cover claims associated with the identified event, to identify those type of policies in the policy information, and to determine whether the identified policies are likely to cover the claim by comparing the policy provisions to the claim information. The training of the coverage prediction model 415 may be further refined by providing feedback on the predictions generated by the model. The coverage prediction model 415 may be trained to take into account coverage limitations and how much of the claim limits have already been utilized by the user when making recommendations. If the policy limits have already been reached for the policy with a first insurer, the coverage prediction model 415 may provide a prediction that the first insurer may not cover the claim or that a second insurer (if available) may cover the claim based on the policies held the insured.

The coverage prediction model 415 may provide a coverage prediction for a group of claims that includes a confidence score representing how confident the model is in the prediction. The submission recommendation unit 405 may be configured to perform various actions in response to the confidence score. As discussed with respect to FIG. 2, the prediction may be assigned a high, medium, or low confidence score by the claim eligibility engine 325. The submission recommendation unit 405 may be configured to assign a confidence level to a prediction provided by the coverage prediction model 415 by comparing the confidence level to a set of thresholds including a first threshold and a second threshold. The first threshold is higher than the second threshold. A confidence score above the first threshold indicates a high confidence level in the prediction. A confidence score below the first threshold but above the second threshold indicates a medium confidence level in the prediction. A confidence score below the second threshold indicates a low confidence level in the prediction.

For predictions having a low confidence level, the submission recommendation unit 405 may discard the prediction. The submission recommendation unit 405 may also notify to the user that the CAAS 105 was unable to identify a policy associated with the user that would cover the claim or group of claims. The submission recommendation unit 405 may include recommendations to the user for revising the claims and resubmitting the claims so that the claims may be covered by an insurer associated with at least one of the user's insurance policies. The submission recommendation unit 405 may also include information why the claim or group of claims are unlikely to be covered by one of the policies associated with the user. For example, the submission recommendation unit 405 may indicate that the user may have reached their policy limits for the type of claim or claims being submitted. Other types of information may be included by the submission recommendation unit 405 for claims that may have been rejected for other reasons.

For predictions having a medium confidence level, the submission recommendation unit 405 may attempt to obtain additional information that may help to disambiguate whether an insurer may cover a particular claim or group of claims and/or to disambiguate between insurers to which to submit the claims. The disambiguation unit 425 may provide a user interface that may be displayed to a user for presenting a set of dynamic questions that attempt to collect additional information from the user that may be used by the recommendation unit 405 to disambiguate whether a particular insurer may cover a claim or set of claims or to disambiguate between the insurers that may cover the claim or set of claims. The dynamic questions may be used to further clarify aspects of the claim that may have been ambiguous when interpreted by the model.

The disambiguation unit 425 may identify additional data that may be useful for determining whether a particular insurer would or would not cover a particular claim. For example, a user may have a supplemental accident insurance policy that covers medical expenses related to certain types of accidentally injuries. The submission recommendation unit 405 may assign a medium confidence level the prediction that the accidental insurance policy may cover claims by the user. In an attempt to make a more definitive prediction whether the accidental insurance policy may cover the user's claims, the disambiguation unit 425 may be configured to request additional details related to the claim that may indicate whether the accidental insurance policy may cover the claim.

In one example, the disambiguation unit 425 may present the user with questions to determine whether the claim is associated with an accidental injury, the type of accident that occurred, and/or information related to determine whether the claim was for a person covered by the policy. The disambiguation unit 425 may update the claim information with the additional information obtained from the user, and the claim may be resubmitted to the coverage prediction model 415 to obtain a new prediction. The process of obtaining additional information and resubmitting the claim to the coverage prediction model 415 may be an iterative process. These steps may be repeated until a prediction is obtained with a high enough confidence level to make an assertion whether the claim is likely to be covered or not be covered by the insurer. An example of such dynamic questions being used to disambiguate whether an insurer may pay a particular claim is shown in FIGS. 6A-6F, which are discussed in detail below.

In another example, the disambiguation unit 425 may ask the user questions that may help to disambiguate between more than one insurer. The coverage prediction model 415 may predict with medium certainty that both a first insurer and a second insurer may potentially cover a particular claim. The first insurer may be an automobile insurance provider that has provided a policy that includes hospitalization coverage related to automobile accidents. The second insurer may be a medical insurance provider that whose policy covers hospitalization for certain illnesses. The disambiguation unit 415 may obtain additional information from the user about the claim or claims and resubmit the claim to the coverage prediction model 415 to obtain a new prediction. For example, the disambiguation unit 425 may present questions to the user related to whether the claims were associated with an automobile accident, whether the claim was for the user or someone else, and/or other information that may help the disambiguation unit 425 make a determination whether the automobile insurance policy or the medical insurance policy may cover the claim. The process may be repeated until the disambiguation unit 425 can obtain a prediction that one of the insurers are likely to cover the claim or that none of the insurers are likely to cover the claim.

For claims having a high confidence level, the submission recommendation unit 405 may present claim submission recommendations to the user via the claim submission assistance unit 420. The claims submission assistance unit 420 may present a summary of the claims to be submitted, an indication of the payer to which the claims are to be submitted, information indicating how much may be reimbursed by the insurer, and instructions for submitting the claims if the claims cannot be submitted electronically by the claim submission assistance unit 420. The claims submission assistance unit 420 may assist the user in filling out claim forms and/or pre-filling claim forms required for submission for claims that cannot be electronically submitted. The user may print the claim forms and submit the physical copies of the claim forms to their insurer for processing.

The model update unit 430 may be configured to provide feedback to the claims grouping model 410 and the coverage prediction model 415 to refine the training of the models. The model update unit 430 may receive feedback directly from the user and/or from the claim submission assistance unit 420. Feedback from the user may be obtained from the claim submission assistance unit 420 in response to the claim submission assistance unit 420 presenting the claim grouping information and insurer information to which the claims submission assistance unit 420 proposes submitting the claims to for reimbursement. The user may indicate that the prediction of the claims grouping is incorrect. The user interface may provide a means for the user to provide an indication of the type of event with which the claims should have been associated. The claims submission assistance unit 420 may also receive a response from an insurer that one or more claims submitted to the insurer have been rejected. The claims submission assistance unit 420 may obtain an EOB or other indication that the one or more claims have been denied by an insurer. The model update unit 430 may be configured to identify a reason that the claims have been rejected. The model update unit 430 may update the coverage prediction model in response to the claims being denied to further fine tune the performance of the coverage prediction model 415.

FIGS. 6A-6F are diagrams showing an example user interface of the CAAS 105. The user interfaces shown in FIGS. 6A-6F may be rendered by a browser application or a native application installed on a client device, such as the client devices 115a-115c shown in FIG. 1. The CAAS 105 may be configured to provide content renderable by a web browser installed on the client device. The CAAS 105 may also be configured to provide content to a native application installed on the client device which is configured to render the content received from the CAAS 105, to allow a user to interact with the content, and to receive requests for data and/or to perform various operations on the data maintained by the CAAS 105.

FIG. 6A is a diagram of a claims overview user interface 605. The claims overview user interface 605 may be implemented by the claims concierge unit 255 of the insights layer 290 of the CAAS 105. The claims overview user interface 605 includes a notification pane 625, a claims details pane 630, and a claims analytics pane 635. The example implementation of the claims overview interface shown in FIG. 6A shows one possible implementation of such an interface. Other implementations may present additional information to the user instead of or in addition to the information provided in this example.

The claims details pane 630 provides details of claims that were recently submitted to one or more insurers on behalf of the insured. The claims details may indicate who was covered, such as a member of the family of the insured user, when a particular service was performed, what service was performed, copay information, insurer information for the insurer to which the claim was filed, and/or other information related to the claims made to the insurer's policy. The claims information may be obtained from the plan metadata 215, the data lake 210, and/or another persistent data storage area of the raw data layer 205 of the CAAS 105. The claims details pane 630 may be configured to enable the user to obtain additional information for a claim by clicking on a link or other user interface component that may be clicked or otherwise activated by the user.

The claims analytics pane 635 may present information reporting various aspects of the user's insurance plan usage. The analytics may include information for multiple policy types, copays and other out-of-pocket spending by the user, and/or other information related to the user's usage of their insurance policies. The claims analytics pane 635 may be configured to enable the user to obtain additional information for various elements of the analytics data by clicking on a link or other user interface component that may be clicked or otherwise activated by the user.

The notification pane 625 may be used to present informational messages to a user regarding their account information, policy information, claims information, or a combination thereof. The notification pane 625 may also include a link, button, or other means for activating functionality associated with the content presented in the notification pane 625. In the implementation shown in FIG. 6A, the notification pane 625 shows a message that indicates that the user may be able to submit a claim to her insurance company.

FIG. 6B shows a user interface 610 that may be displayed in response to the user clicking on or otherwise activating the link, button, or other means for activating functionality associated with the content presented in the notification pane 625. The user interface 610 shows details of a claim that the CAAS 105 has identified as potentially being covered by the user's accident insurance policy. The CAAS 105 may be configured to automatically analyze unpaid claims and/or claims for which the user has not been fully reimbursed to determine whether any of the user's insurance policies may cover these claims. In other implementations, the user may select a claim which the user would like to have the CAAS 105 analyze and present recommendations for submitting the claims to an insurer. The user may click the "Begin" button to indicate to the CAAS 105 that the user would like to be guided through the submission process for the claim.

FIG. 6C shows a user interface 615 that provides details of the claim. The user may review information for the provider that provided the services associated with the claim, the date of these services, costs already reimbursed by an insurer, copay information paid by the user, and/or other information. In the example shown in FIG. 6C, the user's medical insurance covered most of the claim costs, but the user was still required to pay a portion of the costs. In other implementations, the claim may have been rejected and nothing may have been paid by an insurer. In other implementations, the claim may not yet have been submitted to an insurer. The user may click the "Back" button to return to user interface 610 or the "Next" button to advance to the user interface 620 shown in FIG. 6D.

The example user interface 620 shown in FIGS. 6D-6F presents a series of questions to the user to collect additional information from the user that may be used to disambiguate whether a particular insurer may pay a particular claim or to disambiguate between two insurers. The user interface 620 may present a question to the user and be configured to receive a user input in response to the question. The questions may be presented by the disambiguation unit 425, and the information collected may be used to update the claims information maintained by the CAAS 105. The submission recommendation unit 405 of the claim processing engine 325 may process the claim to obtain a prediction whether one of the user's policies is likely to cover the claim. If the claim processing engine 325 predicts that the claim may be covered by a policy, the user interface 620 may guide the user through the steps of submitting the claim to the insurer.

Figure 7:
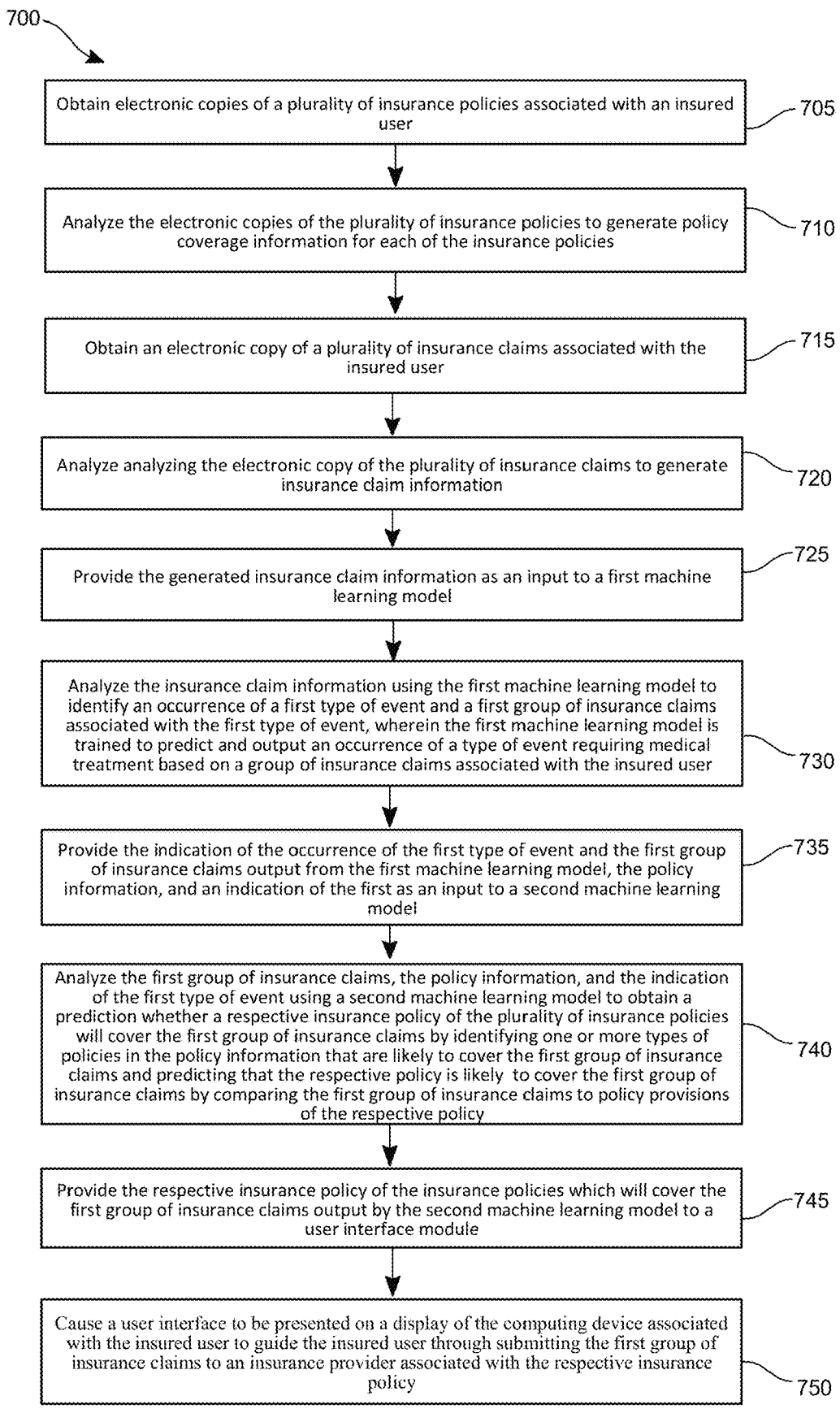
FIG. 7 is a flow chart of an example process for claims analysis adjudication.

FIG. 7 is a flow chart of an example process 700 for insurance claims analysis and adjudication. The process 700 may be implemented by the CAAS 105 discussed in the preceding examples.

The process 700 may include an operation 705 of obtaining electronic copies of a plurality of insurance policies associated with an insured user. As discussed in the preceding examples, the raw data layer 205 of the CAAS 105 may obtain electronic copies of the insurance provider documents from the insurers via the insurer portals 125. The raw policy data may be stored in the data lake 210 of the raw data layer. The raw policy data may be received in a Portable Document Format (PDF), a text file, a scanned image of the policy documents, or other electronic format.

The process 700 may include an operation 710 of analyzing the electronic copies of the plurality of insurance policies to generate policy coverage information for each of the insurance policies. The policy parsing engine 315 may be configured to analyze the electronic copies of the plurality of insurance policies and to extract policy coverage information from the electronic copies of the insurance policies. The policy parsing engine 315 may be configured to perform optical character recognition on the electronic copies of the policies if the electronic copies are not in a text-based format. The policy parsing engine 315 may also be configured to parse the electronic copies of the documents to extract the textual provisions of the insurance policies and to reformat those policies into a standard schema that is used by the CAAS 105. Different insurers may have different formats for their insurance policies, and the policy parsing engine 315 can map the data from those formats into the standard schema used by the CAAS 105. Normalizing the policy data into such a standardized schema may facilitate training of the machine learning models used to analyze the policy data, because the models do not need to recognize the many possible ways in which the insurers may organize the policy data in the insurance policies. As discussed in the preceding examples, the policy parsing engine 315 may also be configured to standardize the policy coverage information included in the insurances policies in addition to standardizing the format of the policy coverage information. The policy parsing engine 315 may be configured to use fuzzy matching to match standardized descriptions of insurance coverage provisions with the coverage information included in the policy. The insurers may not use different language to describe the same type of coverage being provided by a provision of an insurance policy. By standardizing the description of the policy provisions, the machine learning models used by the CAAS 105 may be more likely to correctly predict whether a particular insurance policy may cover a particular insurance claim.

The process 700 may include an operation 715 of obtaining an electronic copy of a plurality of insurance claims associated with the insured user. The raw data layer 205 of the CAAS 105 may obtain electronic insurance claims information from the insurers via the claims and policy API 240. The claims data may be obtained in substantially real time from the insurers via the insurer portals 125. The claims data may include information related to procedures performed for an insured party and/or prescription information that were prescribed for an insured party. The claims information and the prescription information may be submitted to the insurers via the service provider portals 135, which may provide a means for doctors, dentists, optometrists, and/or other medical professionals to submit claims to the insurers on behalf of the insured user. The claims may be submitted on behalf of the insured user and/or other parties covered by the insurance policies.

The process 700 may include an operation 720 of analyzing the electronic copy of the plurality of insurance claims to generate insurance claim information. The policy parsing engine 315 of the CAAS 105 may be configured to use fuzzy matching to match standardized descriptions of procedures performed and/or other information included in the claims. The medical providers providing the services may describe the same procedure in an inconsistent manner that may make determining whether the insured user has a policy that covers the claim more difficult. By standardizing the description of the claims, the machine learning models used by the CAAS 105 may be more likely to correctly predict whether a particular insurance policy may cover that claim.

The process 700 may include an operation 725 of providing the generated insurance claim information as an input to a first machine learning model, and operation 730 of analyzing the insurance claim information using the first machine learning model to identify an occurrence of a first type of event and a first group of insurance claims associated with the first type of event, wherein the first machine learning model is trained to predict and output an occurrence of a type of event requiring medical treatment based on a group of insurance claims associated with the insured user, and an operation 735 of providing the indication of the occurrence of the first type of event and the first group of insurance claims output from the first machine learning model, the policy information, and an indication of the first as an input to a second machine learning model. The claim eligibility engine 325 may be configured to analyze the insurance claim information using one or more machine learning models. As shown in FIG. 4, the claim eligibility engine 325 may submit multiple claims to the claims grouping model 410 to obtain predictions where the groups of claims may be analyzed to determine whether the claims are indicative of a particular event, such as but not limited to a sports injury or an automobile accident that may have resulted in medical claims for the insured user. The output of the claims grouping model 410 may be provided to the coverage prediction model 415 as input.

The process 700 may include an operation 740 of analyzing the first group of insurance claims, the policy information, and the indication of the first type of event using a second machine learning model to obtain a prediction whether a respective insurance policy of the plurality of insurance policies will cover the first group of insurance claims by identifying one or more types of policies in the policy information that are likely to cover the first group of insurance claims and predicting that the respective policy is likely to cover the first group of insurance claims by comparing the first group of insurance claims to policy provisions of the respective policy. As shown in FIG. 4, the claim eligibility engine 325 may analyze the insurance claim information using the coverage prediction model 415 to obtain a prediction whether a particular insurer is likely to cover a group of insurance claims. The model may analyze insurance policies associated with multiple insurers and provide a prediction of an insurer of the plurality of insurers that is most likely to cover the group of claims.

The process 700 may include an operation 745 of providing the respective insurance policy of the insurance policies which will cover the first group of insurance claims output by the second machine learning model to a user interface module and an operation 750 of causing a user interface to be presented on a display of the computing device associated with the insured user to guide the insured user through submitting the first group of insurance claims to an insurance provider associated with the respective insurance policy. The CAAS 105 may implement a user interface module that may be configured to present a user interface for providing recommendations for submitting the claims to a particular insurer based on the predictions by the coverage prediction model 415. The CAAS 105 may present a user interface that guides the user through inputting information for the claim and submitting the claims online to the insurer via the insurer portals 125. In other instances, the CAAS 105 may guide the insured user through filling out forms that may be submitted to the insurer by the insured user. The CAAS 105 may assist the user by prefilling in at least a portion of the information included on the forms, and the insured user may print out a copy of the forms to provide to the insurer. The CAAS 105 may store information indicating the data formats required for submitting data to each of the insurers in the raw data layer 205 and may include one or more formatting engines (not shown) that are configured to format the data stored in the standard schema to the data format expected by the insurer to which the claims are being submitted.

The detailed examples of systems, devices, and techniques described in connection with FIGS. 1-7 are presented herein for illustration of the disclosure and its benefits. Such examples of use should not be construed to be limitations on the logical process embodiments of the disclosure, nor should variations of user interface methods from those described herein be considered outside the scope of the present disclosure. It is understood that references to displaying or presenting an item (such as, but not limited to, presenting an image on a display device, presenting audio via one or more loudspeakers, and/or vibrating a device) include issuing instructions, commands, and/or signals causing, or reasonably expected to cause, a device or system to display or present the item. In some embodiments, various features described in FIGS. 1-7 are implemented in respective modules, which may also be referred to as, and/or include, logic, components, units, and/or mechanisms. Modules may constitute either software modules (for example, code embodied on a machine-readable medium) or hardware modules.

In some examples, a hardware module may be implemented mechanically, electronically, or with any suitable combination thereof. For example, a hardware module may include dedicated circuitry or logic that is configured to perform certain operations. For example, a hardware module may include a special-purpose processor, such as a field-programmable gate array (FPGA) or an Application Specific Integrated Circuit (ASIC). A hardware module may also include programmable logic or circuitry that is temporarily configured by software to perform certain operations and may include a portion of machine-readable medium data and/or instructions for such configuration. For example, a hardware module may include software encompassed within a programmable processor configured to execute a set of software instructions. It will be appreciated that the decision to implement a hardware module mechanically, in dedicated and permanently configured circuitry, or in temporarily configured circuitry (for example, configured by software) may be driven by cost, time, support, and engineering considerations.

Accordingly, the phrase "hardware module" should be understood to encompass a tangible entity capable of performing certain operations and may be configured or arranged in a certain physical manner, be that an entity that is physically constructed, permanently configured (for example, hardwired), and/or temporarily configured (for example, programmed) to operate in a certain manner or to perform certain operations described herein. As used herein, "hardware-implemented module" refers to a hardware module. Considering examples in which hardware modules are temporarily configured (for example, programmed), each of the hardware modules need not be configured or instantiated at any one instance in time. For example, where a hardware module includes a programmable processor configured by software to become a special-purpose processor, the programmable processor may be configured as respectively different special-purpose processors (for example, including different hardware modules) at different times. Software may accordingly configure a processor or processors, for example, to constitute a particular hardware module at one instance of time and to constitute a different hardware module at a different instance of time. A hardware module implemented using one or more processors may be referred to as being "processor implemented" or "computer implemented."

Hardware modules can provide information to, and receive information from, other hardware modules. Accordingly, the described hardware modules may be regarded as being communicatively coupled. Where multiple hardware modules exist contemporaneously, communications may be achieved through signal transmission (for example, over appropriate circuits and buses) between or among two or more of the hardware modules. In embodiments in which multiple hardware modules are configured or instantiated at different times, communications between such hardware modules may be achieved, for example, through the storage and retrieval of information in memory devices to which the multiple hardware modules have access. For example, one hardware module may perform an operation and store the output in a memory device, and another hardware module may then access the memory device to retrieve and process the stored output.

In some examples, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by, and/or among, multiple computers (as examples of machines including processors), with these operations being accessible via a network (for example, the Internet) and/or via one or more software interfaces (for example, an application program interface (API)). The performance of certain of the operations may be distributed among the processors, not only residing within a single machine, but deployed across several machines. Processors or processor-implemented modules may be in a single geographic location (for example, within a home or office environment, or a server farm), or may be distributed across multiple geographic locations.

Figure 8:
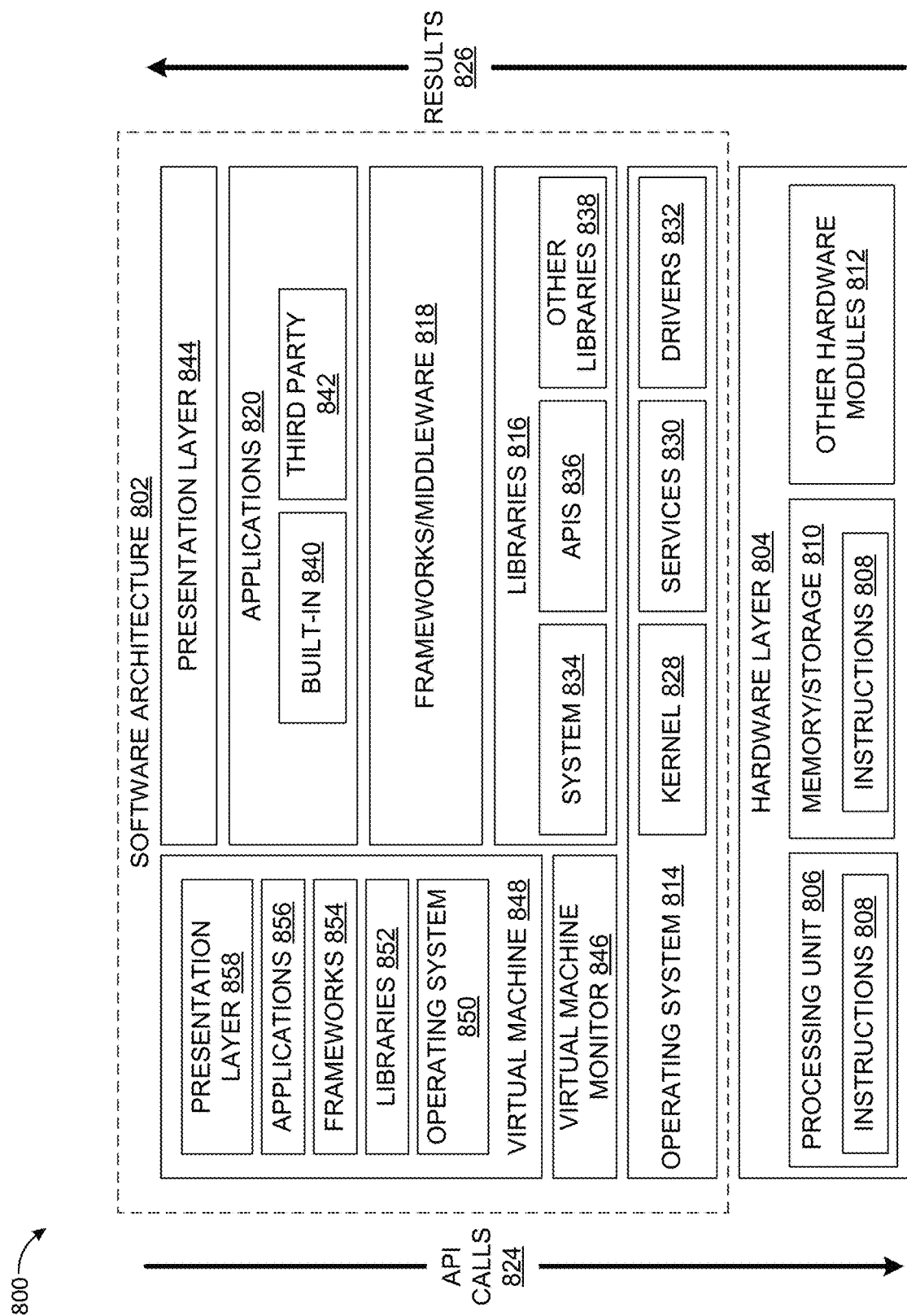
FIG. 8 is a block diagram showing an example software architecture, various portions of which may be used in conjunction with various hardware architectures herein described, which may implement any of the described features.

FIG. 8 is a block diagram 800 illustrating an example software architecture 802, various portions of which may be used in conjunction with various hardware architectures herein described, which may implement any of the above-described features. FIG. 8 is a non-limiting example of a software architecture and it will be appreciated that many other architectures may be implemented to facilitate the functionality described herein. The software architecture 802 may execute on hardware such as a machine 900 of FIG. 9 that includes, among other things, processors 910, memory 930, and input/output (I/O) components 950. A representative hardware layer 804 is illustrated and can represent, for example, the machine 900 of FIG. 9. The representative hardware layer 804 includes a processing unit 806 and associated executable instructions 808. The executable instructions 808 represent executable instructions of the software architecture 802, including implementation of the methods, modules and so forth described herein. The hardware layer 804 also includes a memory/storage 810, which also includes the executable instructions 808 and accompanying data. The hardware layer 804 may also include other hardware modules 812. Instructions 808 held by processing unit 806 may be portions of instructions 808 held by the memory/storage 810.

The example software architecture 802 may be conceptualized as layers, each providing various functionality. For example, the software architecture 802 may include layers and components such as an operating system (OS) 814, libraries 816, frameworks 818, applications 820, and a presentation layer 844. Operationally, the applications 820 and/or other components within the layers may invoke API calls 824 to other layers and receive corresponding results 826. The layers illustrated are representative in nature and other software architectures may include additional or different layers. For example, some mobile or special purpose operating systems may not provide the frameworks/middleware 818.

The OS 814 may manage hardware resources and provide common services. The OS 814 may include, for example, a kernel 828, services 830, and drivers 832. The kernel 828 may act as an abstraction layer between the hardware layer 804 and other software layers. For example, the kernel 828 may be responsible for memory management, processor management (for example, scheduling), component management, networking, security settings, and so on. The services 830 may provide other common services for the other software layers. The drivers 832 may be responsible for controlling or interfacing with the underlying hardware layer 804. For instance, the drivers 832 may include display drivers, camera drivers, memory/storage drivers, peripheral device drivers (for example, via Universal Serial Bus (USB)), network and/or wireless communication drivers, audio drivers, and so forth depending on the hardware and/or software configuration.

The libraries 816 may provide a common infrastructure that may be used by the applications 820 and/or other components and/or layers. The libraries 816 typically provide functionality for use by other software modules to perform tasks, rather than rather than interacting directly with the OS 814. The libraries 816 may include system libraries 834 (for example, C standard library) that may provide functions such as memory allocation, string manipulation, file operations. In addition, the libraries 816 may include API libraries 836 such as media libraries (for example, supporting presentation and manipulation of image, sound, and/or video data formats), graphics libraries (for example, an OpenGL library for rendering 2D and 3D graphics on a display), database libraries (for example, SQLite or other relational database functions), and web libraries (for example, WebKit that may provide web browsing functionality). The libraries 816 may also include a wide variety of other libraries 838 to provide many functions for applications 820 and other software modules.

The frameworks 818 (also sometimes referred to as middleware) provide a higher-level common infrastructure that may be used by the applications 820 and/or other software modules. For example, the frameworks 818 may provide various graphic user interface (GUI) functions, high-level resource management, or high-level location services. The frameworks 818 may provide a broad spectrum of other APIs for applications 820 and/or other software modules.

The applications 820 include built-in applications 840 and/or third-party applications 842. Examples of built-in applications 840 may include, but are not limited to, a contacts application, a browser application, a location application, a media application, a messaging application, and/or a game application. Third-party applications 842 may include any applications developed by an entity other than the vendor of the particular platform. The applications 820 may use functions available via OS 814, libraries 816, frameworks 818, and presentation layer 844 to create user interfaces to interact with users.

Some software architectures use virtual machines, as illustrated by a virtual machine 848. The virtual machine 848 provides an execution environment where applications/ modules can execute as if they were executing on a hardware machine (such as the machine 900 of FIG. 9, for example). The virtual machine 848 may be hosted by a host OS (for example, OS 814) or hypervisor, and may have a virtual machine monitor 846 which manages operation of the virtual machine 848 and interoperation with the host operating system. A software architecture, which may be different from software architecture 802 outside of the virtual machine, executes within the virtual machine 848 such as an OS 850, libraries 852, frameworks 854, applications 856, and/or a presentation layer 858.

Figure 9:
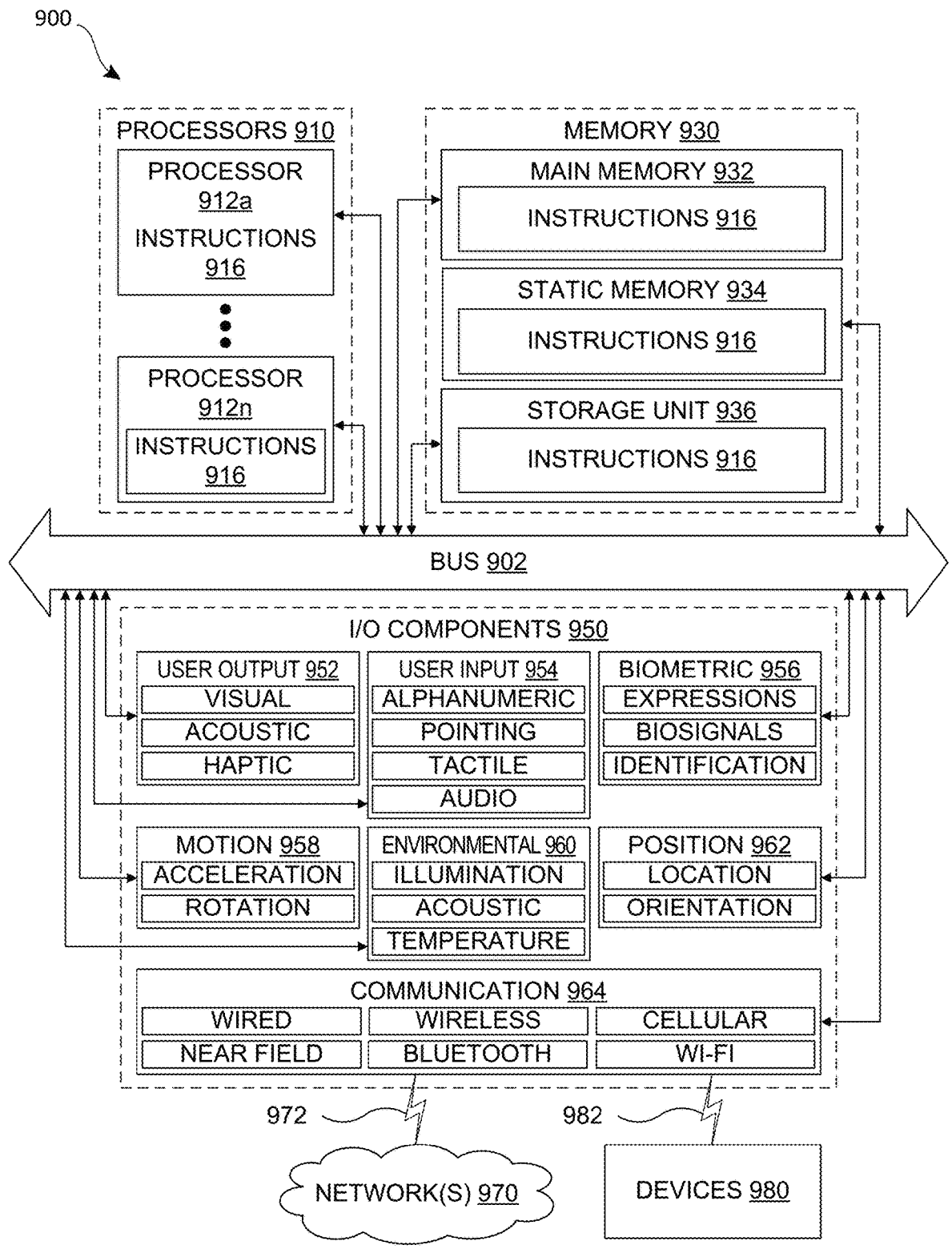
FIG. 9 is a block diagram showing components of an example machine configured to read instructions from a machine-readable medium and perform any of the features described herein.

FIG. 9 is a block diagram illustrating components of an example machine 900 configured to read instructions from a machine-readable medium (for example, a machine-readable storage medium) and perform any of the features described herein. The example machine 900 is in a form of a computer system, within which instructions 916 (for example, in the form of software components) for causing the machine 900 to perform any of the features described herein may be executed. As such, the instructions 916 may be used to implement modules or components described herein. The instructions 916 cause unprogrammed and/or unconfigured machine 900 to operate as a particular machine configured to carry out the described features. The machine 900 may be configured to operate as a standalone device or may be coupled (for example, networked) to other machines. In a networked deployment, the machine 900 may operate in the capacity of a server machine or a client machine in a server-client network environment, or as a node in a peer-to-peer or distributed network environment. Machine 900 may be embodied as, for example, a server computer, a client computer, a personal computer (PC), a tablet computer, a laptop computer, a netbook, a set-top box (STB), a gaming and/or entertainment system, a smart phone, a mobile device, a wearable device (for example, a smart watch), and an Internet of Things (IoT) device. Further, although only a single machine 900 is illustrated, the term "machine" includes a collection of machines that individually or jointly execute the instructions 916.

The machine 900 may include processors 910, memory 930, and I/O components 950, which may be communicatively coupled via, for example, a bus 902. The bus 902 may include multiple buses coupling various elements of machine 900 via various bus technologies and protocols. In an example, the processors 910 (including, for example, a central processing unit (CPU), a graphics processing unit (GPU), a digital signal processor (DSP), an ASIC, or a suitable combination thereof) may include one or more processors 912a to 912n that may execute the instructions 916 and process data. In some examples, one or more processors 910 may execute instructions provided or identified by one or more other processors 910. The term "processor" includes a multi-core processor including cores that may execute instructions contemporaneously. Although FIG. 9 shows multiple processors, the machine 900 may include a single processor with a single core, a single processor with multiple cores (for example, a multi-core processor), multiple processors each with a single core, multiple processors each with multiple cores, or any combination thereof. In some examples, the machine 900 may include multiple processors distributed among multiple machines.

The memory/storage 930 may include a main memory 932, a static memory 934, or other memory, and a storage unit 936, both accessible to the processors 910 such as via the bus 902. The storage unit 936 and memory 932, 934 store instructions 916 embodying any one or more of the functions described herein. The memory/storage 930 may also store temporary, intermediate, and/or long-term data for processors 910. The instructions 916 may also reside, completely or partially, within the memory 932, 934, within the storage unit 936, within at least one of the processors 910 (for example, within a command buffer or cache memory), within memory at least one of I/O components 950, or any suitable combination thereof, during execution thereof. Accordingly, the memory 932, 934, the storage unit 936, memory in processors 910, and memory in I/O components 950 are examples of machine-readable media.

As used herein, "machine-readable medium" refers to a device able to temporarily or permanently store instructions and data that cause machine 900 to operate in a specific fashion, and may include, but is not limited to, random-access memory (RAM), read-only memory (ROM), buffer memory, flash memory, optical storage media, magnetic storage media and devices, cache memory, network-accessible or cloud storage, other types of storage and/or any suitable combination thereof. The term "machine-readable medium" applies to a single medium, or combination of multiple media, used to store instructions (for example, instructions 916) for execution by a machine 900 such that the instructions, when executed by one or more processors 910 of the machine 900, cause the machine 900 to perform and one or more of the features described herein. Accordingly, a "machine-readable medium" may refer to a single storage device, as well as "cloud-based" storage systems or storage networks that include multiple storage apparatus or devices. The term "machine-readable medium" excludes signals per se.

The I/O components 950 may include a wide variety of hardware components adapted to receive input, provide output, produce output, transmit information, exchange information, capture measurements, and so on. The specific I/O components 950 included in a particular machine will depend on the type and/or function of the machine. For example, mobile devices such as mobile phones may include a touch input device, whereas a headless server or IoT device may not include such a touch input device. The particular examples of I/O components illustrated in FIG. 9 are in no way limiting, and other types of components may be included in machine 900. The grouping of I/O components 950 are merely for simplifying this discussion, and the grouping is in no way limiting. In various examples, the I/O components 950 may include user output components 952 and user input components 954. User output components 952 may include, for example, display components for displaying information (for example, a liquid crystal display (LCD) or a projector), acoustic components (for example, speakers), haptic components (for example, a vibratory motor or force-feedback device), and/or other signal generators. User input components 954 may include, for example, alphanumeric input components (for example, a keyboard or a touch screen), pointing components (for example, a mouse device, a touchpad, or another pointing instrument), and/or tactile input components (for example, a physical button or a touch screen that provides location and/or force of touches or touch gestures) configured for receiving various user inputs, such as user commands and/or selections.

In some examples, the I/O components 950 may include biometric components 956, motion components 958, environmental components 960, and/or position components 962, among a wide array of other physical sensor components. The biometric components 956 may include, for example, components to detect body expressions (for example, facial expressions, vocal expressions, hand or body gestures, or eye tracking), measure biosignals (for example, heart rate or brain waves), and identify a person (for example, via voice-, retina-, fingerprint-, and/or facial-based identification). The motion components 958 may include, for example, acceleration sensors (for example, an accelerometer) and rotation sensors (for example, a gyroscope). The environmental components 960 may include, for example, illumination sensors, temperature sensors, humidity sensors, pressure sensors (for example, a barometer), acoustic sensors (for example, a microphone used to detect ambient noise), proximity sensors (for example, infrared sensing of nearby objects), and/or other components that may provide indications, measurements, or signals corresponding to a surrounding physical environment. The position components 962 may include, for example, location sensors (for example, a Global Position System (GPS) receiver), altitude sensors (for example, an air pressure sensor from which altitude may be derived), and/or orientation sensors (for example, magnetometers).

The I/O components 950 may include communication components 964, implementing a wide variety of technologies operable to couple the machine 900 to network(s) 970 and/or device(s) 980 via respective communicative couplings 972 and 982. The communication components 964 may include one or more network interface components or other suitable devices to interface with the network(s) 970. The communication components 964 may include, for example, components adapted to provide wired communication, wireless communication, cellular communication, Near Field Communication (NFC), Bluetooth communication, Wi-Fi, and/or communication via other modalities. The device(s) 980 may include other machines or various peripheral devices (for example, coupled via USB).

In some examples, the communication components 964 may detect identifiers or include components adapted to detect identifiers. For example, the communication components 964 may include Radio Frequency Identification (RFID) tag readers, NFC detectors, optical sensors (for example, one- or multi-dimensional bar codes, or other optical codes), and/or acoustic detectors (for example, microphones to identify tagged audio signals). In some examples, location information may be determined based on information from the communication components 962, such as, but not limited to, geo-location via Internet Protocol (IP) address, location via Wi-Fi, cellular, NFC, Bluetooth, or other wireless station identification and/or signal triangulation.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed is:

1. A data processing system comprising:
a processor; and
a computer-readable medium storing executable instructions that, when executed, cause the processor to perform operations comprising:
obtaining electronic copies of a plurality of insurance policies associated with an insured user;
analyzing the electronic copies of the plurality of insurance policies to generate policy coverage information for each of the insurance policies;
converting the policy coverage information from a first format to a second format to generate standardized policy coverage information, the second format being associated with a standard schema for processing policy and claim information;
obtaining an electronic copy of a plurality of insurance claims associated with the insured user;
analyzing the electronic copy of the plurality of insurance claims to generate insurance claim information;
converting the insurance claim information from a third format to a fourth format to generate standardized insurance claim information, the fourth format being associated with the standard schema for processing policy and claim information;
providing the standardized insurance claim information as an input to a first machine learning model;
analyzing the standardized insurance claim information using the first machine learning model to identify an occurrence of a first type of event and a first group of insurance claims associated with the first type of event, wherein the first machine learning model is trained using first training data formatted according to the standard schema to predict and output an occurrence of a type of event requiring medical treatment based on a group of insurance claims associated with the insured user;
providing the indication of the occurrence of the first type of event and the first group of insurance claims output from the first machine learning model, the standardized policy information, and an indication of the first type of event as an input to a second machine learning model;
analyzing the first group of insurance claims, the standardized policy information, and the indication of the first type of event using a second machine learning model to obtain a prediction whether a respective insurance policy of the plurality of insurance policies will cover the first group of insurance claims, the second machine learning model being trained using second training data formatted according to the standard schema, the second machine learning model trained to identify one or more types of policies in the standardized policy information that are likely to cover the first group of insurance claims and predicting that the respective policy is likely to cover the first group of insurance claims by comparing the first group of insurance claims to policy provisions of the respective policy;
providing the respective insurance policy of the insurance policies which will cover the first group of insurance claims output by the second machine learning model to a user interface module; and
causing a user interface to be presented on a display of the computing device associated with the insured user to guide the insured user through submitting the first group of insurance claims to an insurance provider associated with the respective insurance policy.

2. The data processing system of claim 1, wherein the plurality of insurance claims includes a first insurance claim, and wherein to analyze the electronic copy of the plurality of insurance claims to generate the insurance claim information the computer-readable medium includes instructions configured to cause the processor to perform:
performing a fuzzy match on information associated with the first insurance claim with a standard set of claim descriptions to identify a first standard description for the first insurance claim; and
adding the first standard description to the insurance claim information.

3. The data processing system of claim 1, wherein the computer-readable medium includes instructions configured to cause the processor to perform:
analyzing the insurance claim information using the first machine learning model to identify an occurrence of a second type of event and a second group of insurance claims associated with the second type of event.

4. The data processing system of claim 3, wherein the computer-readable medium includes instructions configured to cause the processor to perform:
analyzing the second group of insurance claims, the policy information, and an indication of the second type of event using the second machine learning model to obtain a second prediction whether the respective insurance policy of the plurality of insurance policies will cover the second insurance claim; and
responsive to the first machine learning model predicting that the respective insurance policy will cover the second group of insurance claims, presenting the user interface that provides guidance to the user for submitting the second group of insurance claims to a second insurance provider associated with the respective insurance policy.

5. The data processing system of claim 4, wherein the computer-readable medium includes instructions configured to cause the processor to perform:
responsive to a confidence score associated with the second prediction being less than a first threshold, dynamically generating a set of questions to obtain additional information associated with at least one insurance claim of the first group of insurance claims that may increase the confidence score associated with the second prediction; and
obtaining user response information associated with the dynamically generated set of questions.

6. The data processing system of claim 5, wherein the computer-readable medium includes instructions configured to cause the processor to perform:
analyzing the first group of claims, the standardized policy coverage information, and the user response information with the first machine learning model to obtain a third prediction whether the first group of claims may be covered by the respective insurance policy of the plurality of insurance policies; and
responsive to the second machine learning model predicting that the respective insurance policy will cover the first group of insurance claims, presenting the user interface that provides guidance to the user for submitting the first group of insurance claims to a second insurance provider associated with the respective insurance policy.

7. A method implemented in a data processing system for insurance claims analysis and adjudication, the method comprising:

obtaining electronic copies of a plurality of insurance policies associated with an insured user;

analyzing the electronic copies of the plurality of insurance policies to generate policy coverage information for each of the insurance policies;

converting the policy coverage information from a first format to a second format to generate standardized policy coverage information, the second format being associated with a standard schema for processing policy and claim information;

obtaining an electronic copy of a plurality of insurance claims associated with the insured user;

analyzing the electronic copy of the plurality of insurance claims to generate insurance claim information;

converting the insurance claim information from a third format to a fourth format to generate standardized insurance claim information, the fourth format being associated with the standard schema for processing policy and claim information;

providing the standardized insurance claim information as an input to a first machine learning model;

analyzing the standardized insurance claim information using the first machine learning model to identify an occurrence of a first type of event and a first group of insurance claims associated with the first type of event, wherein the first machine learning model is trained using first training data formatted according to the standard schema to predict and output an occurrence of a type of event requiring medical treatment based on a group of insurance claims associated with the insured user;

providing the indication of the occurrence of the first type of event and the first group of insurance claims output from the first machine learning model, the standardized policy information, and an indication of the first type of event as an input to a second machine learning model;

analyzing the first group of insurance claims, the standardized policy information, and the indication of the first type of event using a second machine learning model to obtain a prediction whether a respective insurance policy of the plurality of insurance policies will cover the first group of insurance claims, the second machine learning model being trained using second training data formatted according to the standard schema, the second machine learning model trained to identify one or more types of policies in the standardized policy information that are likely to cover the first group of insurance claims and predicting that the respective policy is likely to cover the first group of insurance claims by comparing the first group of insurance claims to policy provisions of the respective policy;

providing the respective insurance policy of the insurance policies which will cover the first group of insurance claims output by the second machine learning model to a user interface module; and causing a user interface to be presented on a display of the computing device associated with the insured user to guide the insured user through submitting the first group of insurance claims to an insurance provider associated with the respective insurance policy.

8. The method of claim 7, wherein the plurality of insurance claims includes a first insurance claim, and wherein analyzing the electronic copy of the first insurance claim data to generate the claim information further comprises:

performing a fuzzy match on information associated with the first insurance claim with a standard set of claim descriptions to identify a first standard description for the first insurance claim; and adding the first standard description to the insurance claim information.

9. The method of claim 7, further comprising:

analyzing the insurance claim information using the first machine learning model to identify an occurrence of a second type of event and a second group of insurance claims associated with the second type of event.

10. The method of claim 9, further comprising:

analyzing the second group of insurance claims, the policy information, and an indication of the second type of event using the second machine learning model to obtain a second prediction whether the respective insurance policy of the plurality of insurance policies will cover the second insurance claim; and responsive to the first machine learning model predicting that the respective insurance policy will cover the second group of insurance claims, presenting the user interface that provides guidance to the user for submitting the second group of insurance claims to a second insurance provider associated with the respective insurance policy.

11. The method of claim 10, further comprising:

responsive to a confidence score associated with the second prediction being less than a first threshold, dynamically generating a set of questions to obtain additional information associated with at least one insurance claim of the first group of insurance claims that may increase the confidence score associated with the second prediction; and obtaining user response information associated with the dynamically generated set of questions.

12. The method of claim 11, further comprising:

analyzing the first group of claims, the standardized policy coverage information, and the user response information with the first machine learning model to obtain a third prediction whether the first group of claims may be covered by the respective insurance policy of the plurality of insurance policies; and responsive to the second machine learning model predicting that the respective insurance policy will cover the first group of insurance claims, presenting the user interface that provides guidance to the user for submitting the first group of insurance claims to a second insurance provider associated with the respective insurance policy.

13. A machine-readable medium on which are stored instructions that, when executed, cause a processor of a programmable device to perform operations of:

obtaining electronic copies of a plurality of insurance policies associated with an insured user;

analyzing the electronic copies of the plurality of insurance policies to generate policy coverage information for each of the insurance policies;

converting the policy coverage information from a first format to a second format to generate standardized policy coverage information, the second format being associated with a standard schema for processing policy and claim information;

obtaining an electronic copy of a plurality of insurance claims associated with the insured user;

analyzing the electronic copy of the plurality of insurance claims to generate insurance claim information;

converting the insurance claim information from a third format to a fourth format to generate standardized insurance claim information, the fourth format being associated with the standard schema for processing policy and claim information;

providing the standardized insurance claim information as an input to a first machine learning model;

analyzing the standardized insurance claim information using the first machine learning model to identify an occurrence of a first type of event and a first group of insurance claims associated with the first type of event, wherein the first machine learning model is trained using first training data formatted according to the standard schema to predict and output an occurrence of a type of event requiring medical treatment based on a group of insurance claims associated with the insured user;

providing the indication of the occurrence of the first type of event and the first group of insurance claims output from the first machine learning model, the standardized policy information, and an indication of the first type of event as an input to a second machine learning model;

analyzing the first group of insurance claims, the standardized policy information, and the indication of the first type of event using a second machine learning model to obtain a prediction whether a respective insurance policy of the plurality of insurance policies will cover the first group of insurance claims, the second machine learning model being trained using second training data formatted according to the standard schema, the second machine learning model trained to identify one or more types of policies in the standardized policy information that are likely to cover the first group of insurance claims and predicting that the respective policy is likely to cover the first group of insurance claims by comparing the first group of insurance claims to policy provisions of the respective policy;

providing the respective insurance policy of the insurance policies which will cover the first group of insurance claims output by the second machine learning model to a user interface module; and causing a user interface to be presented on a display of the computing device associated with the insured user to guide the insured user through submitting the first group of insurance claims to an insurance provider associated with the respective insurance policy.

14. The machine-readable medium of claim 13, wherein the plurality of insurance claims includes a first insurance claim, and wherein to analyze the electronic copy of the plurality of insurance claims to generate the insurance claim information the computer-readable storage medium includes instructions configured to cause the processor to perform:

performing a fuzzy match on information associated with the first insurance claim with a standard set of claim descriptions to identify a first standard description for the first insurance claim; and adding the first standard description to the insurance claim information.

15. The machine-readable medium of claim 13, wherein the computer-readable storage medium includes instructions configured to cause the processor to perform:

analyzing the insurance claim information using the first machine learning model to identify an occurrence of a second type of event and a second group of insurance claims associated with the second type of event;

analyzing the second group of insurance claims, the policy information, and an indication of the second type of event using the second machine learning model to obtain a second prediction whether the respective insurance policy of the plurality of insurance policies will cover the second insurance claim; and responsive to the first machine learning model predicting that the respective insurance policy will cover the second group of insurance claims, presenting the user interface that provides guidance to the user for submitting the second group of insurance claims to a second insurance provider associated with the respective insurance policy.

16. The machine-readable medium of claim 15, wherein the computer-readable storage medium includes instructions configured to cause the processor to perform:

responsive to a confidence score associated with the second prediction being less than a first threshold, dynamically generating a set of questions to obtain additional information associated with at least one insurance claim of the first group of insurance claims that may increase the confidence score associated with the second prediction; and obtaining user response information associated with the dynamically generated set of questions.

17. The machine-readable medium of claim 16, wherein the computer-readable storage medium includes instructions configured to cause the processor to perform:

analyzing the first group of claims, the standardized policy coverage information, and the user response information with the first machine learning model to obtain a third prediction whether the first group of claims may be covered by the respective insurance policy of the plurality of insurance policies; and responsive to the second machine learning model predicting that the respective insurance policy will cover the first group of insurance claims, presenting the user interface that provides guidance to the user for submitting the first group of insurance claims to a second insurance provider associated with the respective insurance policy.

\* \* \* \* \*